(12) United States Patent
Osorio

(10) Patent No.: US 10,933,241 B2
(45) Date of Patent: Mar. 2, 2021

(54) SYSTEM AND APPARATUS FOR INCREASING REGULARITY AND/OR PHASE-LOCKING OF NEURONAL ACTIVITY RELATING TO AN EPILEPTIC EVENT

(71) Applicant: Ivan Osorio, Leawood, KS (US)

(72) Inventor: Ivan Osorio, Leawood, KS (US)

(73) Assignee: Flint Hills Scientific, L.L.C., Lawrence, KS (US)

( * ) Notice: Subject to any disclaimer, the term of this patent is extended or adjusted under 35 U.S.C. 154(b) by 443 days.

(21) Appl. No.: 15/843,280

(22) Filed: Dec. 15, 2017

(65) Prior Publication Data

US 2018/0200518 A1     Jul. 19, 2018

Related U.S. Application Data

(60) Division of application No. 14/638,890, filed on Mar. 4, 2015, now Pat. No. 9,889,302, which is a continuation of application No. 13/308,913, filed on Dec. 1, 2011, now Pat. No. 8,989,863, which is a continuation-in-part of application No. 13/280,178, filed on Oct. 24, 2011, now Pat. No. 9,533,147, which is a continuation-in-part of application No. 12/729,093, filed on Mar. 22, 2010, now Pat. No. 8,560,073.

(60) Provisional application No. 61/210,850, filed on Mar. 23, 2009.

(51) Int. Cl.
*A61N 1/36*     (2006.01)
*A61N 1/05*     (2006.01)

(52) U.S. Cl.
CPC ..... *A61N 1/36064* (2013.01); *A61N 1/36139* (2013.01); *A61N 1/36142* (2013.01); *A61N 1/0529* (2013.01); *A61N 1/36114* (2013.01); *A61N 1/36171* (2013.01)

(58) Field of Classification Search
CPC ............ A61N 1/36064; A61N 1/36139; A61N 1/36142; A61N 1/0529; A61N 1/36114; A61N 1/36171
See application file for complete search history.

(56) References Cited

U.S. PATENT DOCUMENTS

2005/0273017 A1 * 12/2005 Gordon ................ A61B 5/16
                                                                  600/544
2009/0124923 A1 *  5/2009 Sackellares ......... A61B 5/7275
                                                                  600/544

\* cited by examiner

*Primary Examiner* — Amanda K Hulbert
*Assistant Examiner* — Natasha Patel
(74) *Attorney, Agent, or Firm* — CF3; Stephen Eisenmann

(57) ABSTRACT

A method, comprising detecting, in at least a first brain region of a patient, an electrical activity relating to an epileptic activity; determining a first regularity index of said electrical activity; and applying at least one first electrical stimulation to at least one neural target of said patient for treating said epileptic event, in response to said first regularity index being within a first range. A non-transitive, computer-readable storage device for storing instructions that, when executed by a processor, perform the method. A medical device system suitable for use in the method.

6 Claims, 13 Drawing Sheets

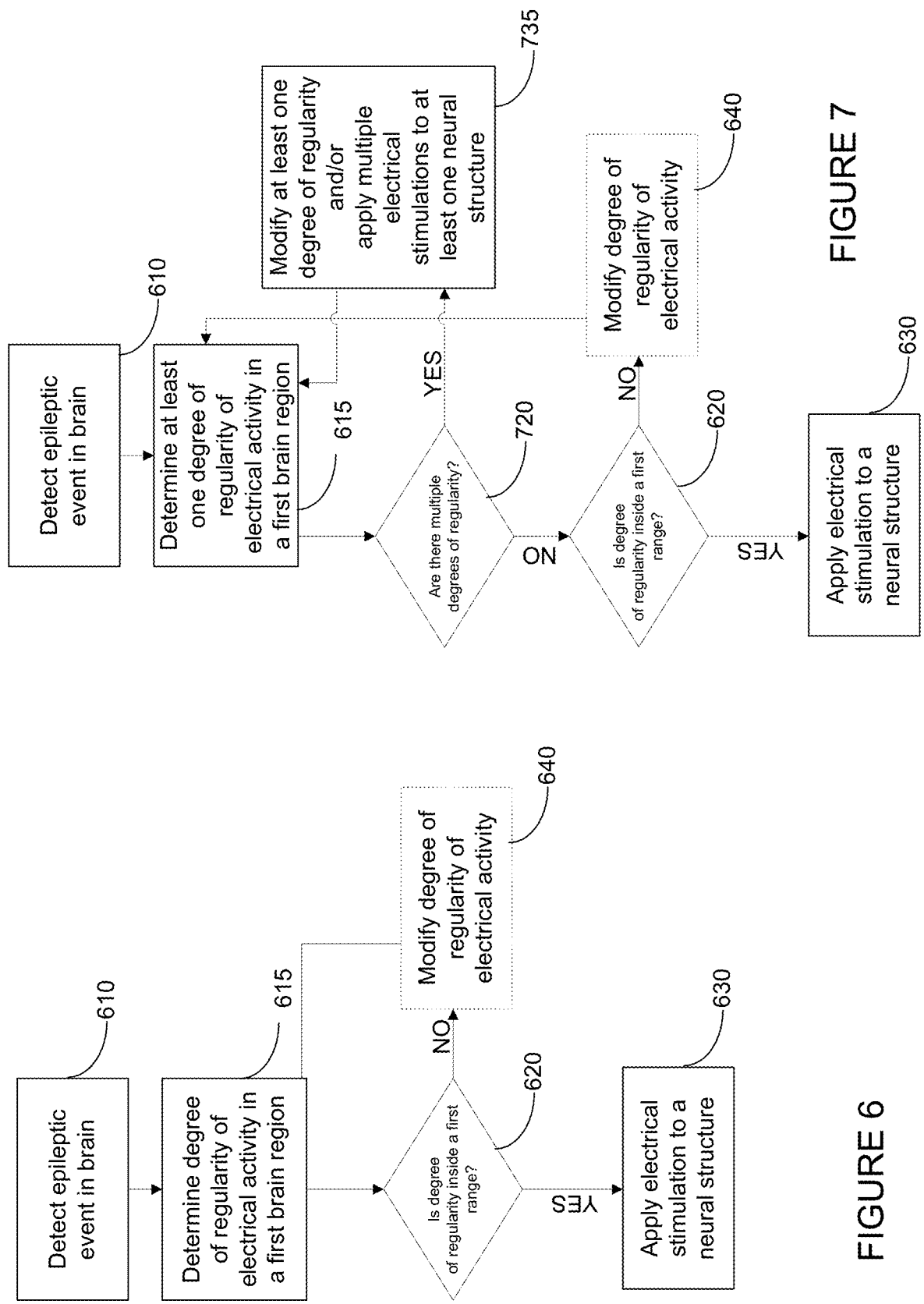

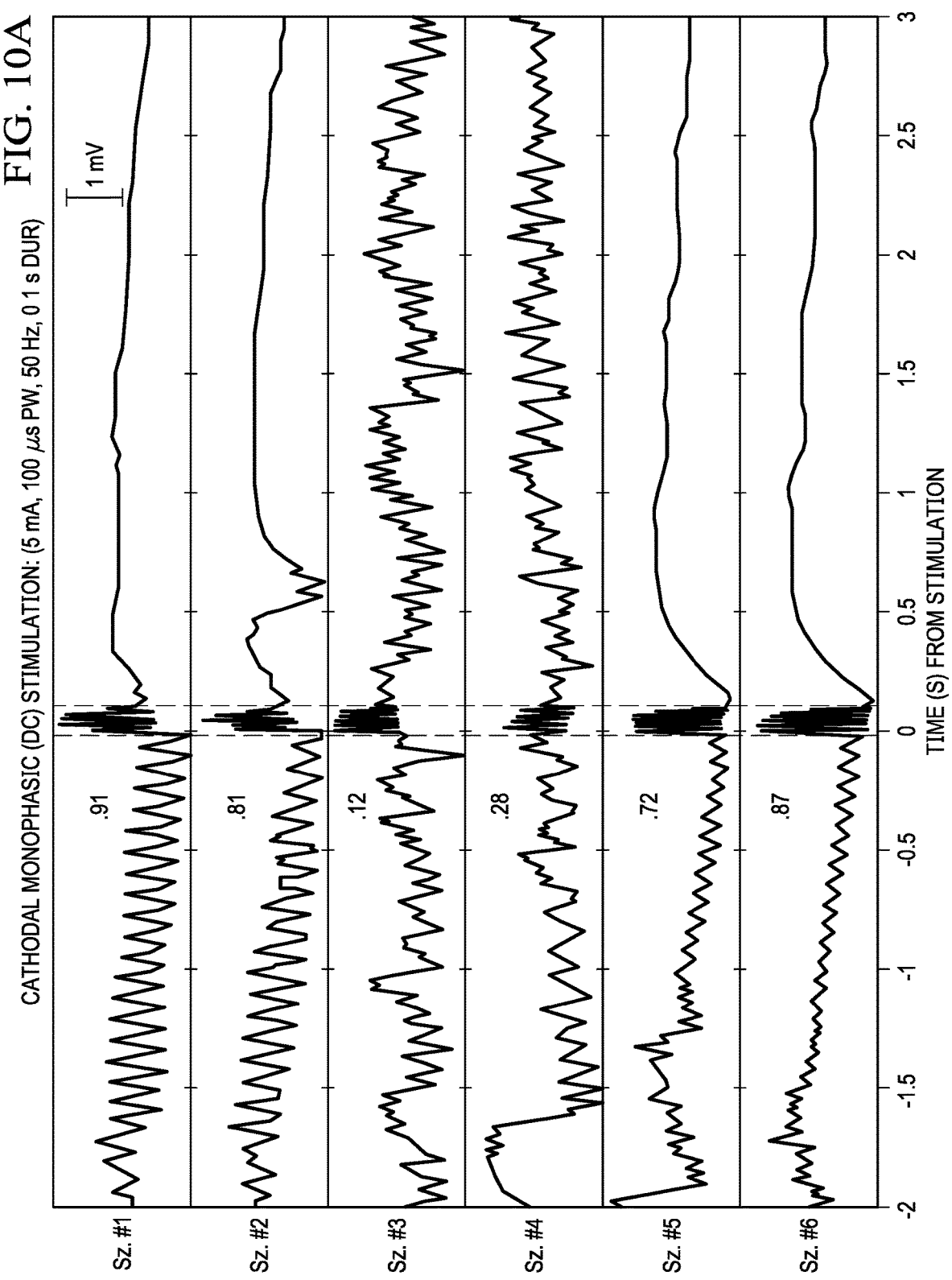

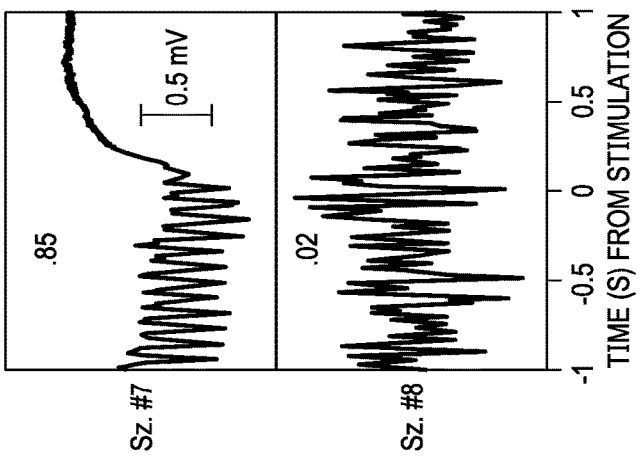
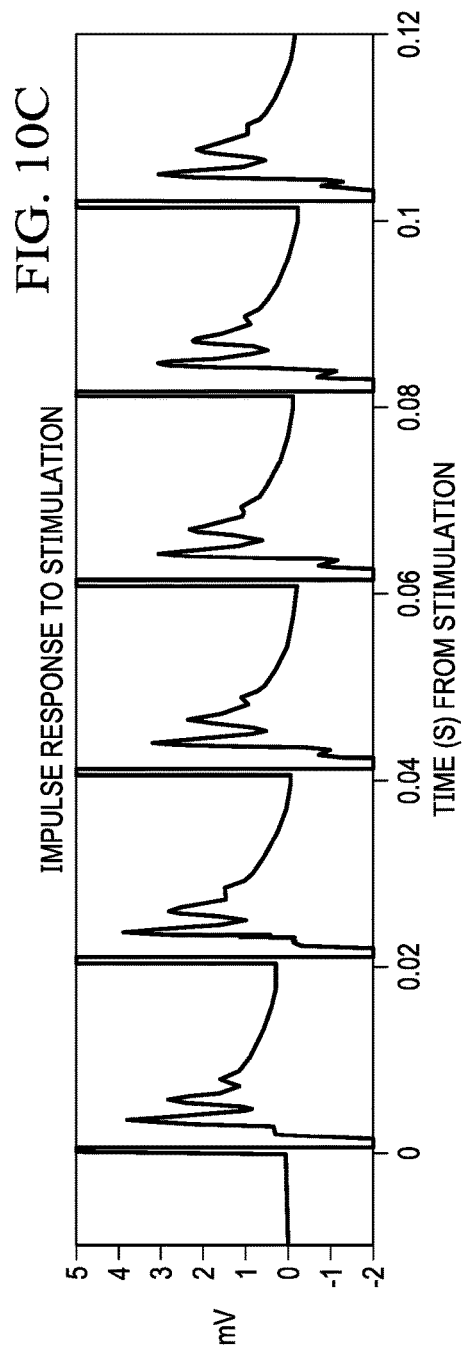

SYSTEM AND APPARATUS FOR INCREASING REGULARITY AND/OR PHASE-LOCKING OF NEURONAL ACTIVITY RELATING TO AN EPILEPTIC EVENT

This application claims priority to and is a divisional application of U.S. patent application Ser. No. 14/638,890, entitled "System and Apparatus for Increasing Regularity and/or Phase-Locking of Neuronal Activity Relating to an Epileptic Event," filed Mar. 4, 2015, which is a continuation of U.S. patent application Ser. No. 13/308,913, entitled "System and Apparatus for Increasing Regularity and/or Phase-Locking of Neuronal Activity Relating to an Epileptic Event," filed Dec. 1, 2011, now U.S. Pat. No. 8,989,863, which is a continuation-in-part of U.S. patent application Ser. No. 13/280,178, entitled "Method, System, and Apparatus for Automated Termination of a Therapy for an Epileptic Event Upon a Determination of Effects of a Therapy," filed Oct. 24, 2011, now U.S. Pat. No. 9,533,147, which is a continuation-in-part of U.S. patent application Ser. No. 12/729,093, entitled "System and Apparatus for Automated Quantitative Assessment, Optimization and Logging of the Effects of a Therapy," filed Mar. 22, 2010, now U.S. Pat. No. 8,560,073, which claimed priority from U.S. Provisional Patent Application No. 61/210,850, entitled "System and Apparatus for Automated Quantitative Assessment, Optimization and Logging of the Effects of a Therapy," filed Mar. 23, 2009. U.S. patent application Ser. Nos. 14/638,890, 13/308,913, 13/280,178; 12/729,093; and 61/210,850 are hereby incorporated herein by reference in their entirety.

Safe and effective therapies for pharmaco-resistant seizures are a major unmet medical need affecting approximately 36% of all epileptics (~1.1 million in the US and ~18 million worldwide). These subjects have poor quality of life, the large majority are unemployed, suffer from depression and are 40 times more likely to die suddenly than age-matched subjects in the general population. Brain electrical stimulation, either directly or indirectly (vagus nerve stimulation), and contingent (triggered by the onset of seizures) or non-contingent (e.g., periodic, round-the-clock), and other therapies such as localized cooling of the epileptogenic zone or direct delivery of drugs to it, hold great promise for these patients. However, in light of the results of large recent clinical trials showing a modest mean decrease in seizure frequency of 40-60% on patients than remain on multiple anti-seizure drugs, optimization is required if they are meet efficaciously and cost-effectively this medical need. This disclosure addresses in a novel, effective, and systematic manner, the complex and demanding task of optimization of interventional brain therapies for control of undesirable changes of state. In its preferred embodiment this disclosure addresses brain state changes and in particular epileptic seizures. Therapies for other neurological (e.g., pain, movement), psychiatric (e.g., mood; obsessive compulsive), and cardiac (e.g., arrhythmias) disorders may be optimized using the approaches described herein.

Epileptic seizures occur with or without discernible or visible clinical manifestations. In the case of seizures originating from discrete brain regions (known as partial or "focal" seizures) the electrical abnormalities usually precede the first clinical manifestation (subjective or objective) and in a large number of these patients, impairment or loss of responsiveness occurs some time after the first clinical manifestation. Also, if the seizure becomes secondarily generalized, loss of consciousness (to be distinguished from loss of responsiveness) occurs after loss of responsiveness. Commonly, abnormal electrical activity outlasts the loss of consciousness and consciousness is regained before responsiveness returns to normal (for the patient) levels. In certain epileptic brains the transition from the non-seizure to the seizure state may be gradual, providing a window for prediction and intervention before the transition is complete. Degree of responsiveness may be tested and quantified in real-time using a wide variety of available tests.

Therapy for control of disorders such as epilepsy which manifest intermittently, aperiodically and briefly (ranging from seconds to rarely >2 min) and are classified as dynamic, meaning that state changes (from normal to abnormal and vice-versa) are caused by changes in the system's control parameter(s) are specially challenging. To increase the probability of therapeutic success local, global, structural, dynamical, and state factors influencing the state change, must be identified and measured with useful precision and at informative time scales. These concepts and considerations required to formulate treatment and optimization strategies are lacking in the state of the art therapies.

While this disclosure is aimed at optimizing a therapy, nothing in its specification precludes delivery of a therapy prior to optimization or without optimization. Indeed, optimization cannot take place if a therapy has not been administered and its effects (beneficial and detrimental) quantified. If a therapy cannot be optimized (in terms of increasing its beneficial effects), optimization may be effected by decreasing the number or intensity and duration of its adverse events. Adverse effects include, but are not limited to, increase in seizure frequency or severity, cognitive impairment in functions such as memory, language, mood (depression or mania), and/or psychosis. These adverse effects may be quantified using cognitive, electrical, thermal, optical and other signals and logged to computer memory. In the case of signals that lack easily detectable or recognizable electrical or other correlates, they may be characterized using a semi-quantitative approach such as psychiatric scales, caregiver observations or patient diaries.

The term "therapy" may be interchangeably used with the term control for which a theory exists (Control Theory) in the field of engineering. Since therapy and control share the same aim, it is appropriate to adopt certain concepts form this theory as well as from the fields of dynamics to generate a rational approach and strategy for the management of pharmaco-resistant seizures.

The epileptic brain may be conceptualized as a non-stationary, non-linear, "noisy" system that undergoes sudden unexplained reversible transitions from the non-seizure state. The manner in which this transition occurs may be "gradual" (through a process of "attractor deformation") or sudden (through a "leap" from one state to another) as observed in bi-stable or multi-stable systems. Dynamical theory teaches that a system may be defined by its dimension (which corresponds to the minimum number of variables required to specify it). The identification of a system's dimension greatly benefits from the identification of a spatio-temporal scale of observation that corresponds to a representative sample of the system (so-called mesoscopic scale), thus obviating the need to study the whole system at all scales, a daunting and impracticable task in the case of the mammalian brain. The epileptic brain's dimensionality and its mesoscopic scale have not been effectively specified to date. This knowledge void forces the treatment of the brain as a "black-box".

While by definition a "black-box" is not amenable to direct inquiry, it can be indirectly studied through perturbations of system inputs. A known, well characterized input is "fed" into the "black-box" and the output is carefully recorded and characterized quantitatively or qualitatively and compared to the input. Transformations, if any to the input properties provide indirect but useful information about the "black-box" that may be captured mathematically as transfer functions. For example, if doubling the amplitude of the input translates into doubling of the output, the system is considered linear. However if doubling the input causes an exponential increase in the output, the system is non-linear (likely the brain's case). If sine waves are fed into the black box and 60 Hz activity appears on them as they exit the box, it is reasonable to infer that the box corrupts the waves and is "noisy". Successful control of the behavior of "black-boxes" cannot occur if the measurements of its output are not representative of the state(s) and site(s) from where they are obtained, reasonably precise and also reproducible from measurement to measurement.

Global and local factors (many state-dependent) also shape the response to therapies. For example, the rate and direction of diffusion of particles and molecules in animal tissue (e.g. brain), depends on multiple factors including size, chemical valence and the size and tortuosity of the extracellular space. In certain tissues, such as the brain's, the average values of the dielectric constant, or permittivity, and of the resistance are not equal at all points of the volume which the particles and molecules occupy. This anisotropy, which varies by a factor of 5-10 between two orthogonally-selected directions, such as between the vertical (or radial) and horizontal (or transverse) directions in a brain's cortex or its axons, ensures that diffusion of endogenous and exogenous (e.g., electrical stimulation) currents is not homogenous. This lack of homogeneity (and of isotropy) in the case of a therapy (e.g., electrical stimulation) that must diffuse through the tissue to exert its beneficial action is likely to decrease efficacy, a feature that must be considered for control and optimization purposes.

The diffusions of electrical currents within the brain, which as vectors have both magnitude (potential) and direction, are the result of electrostatic forces caused by the transient accumulation of charges and also of electrodynamic actions arising from ionic or electronic currents in the volume which surrounds the local accumulations of such charges. Intracortical diffusion of electrical charges (ions) and currents, takes place at several spatial domains or scales (active membrane sites, cells, columns and the cortical synergic groups where they flow differentially through the lattice of intercellular spaces and through the network of glial cells. These flows occur through a large number of routes at their disposal, each route being the path for only a small part of the total current (Kirchhoff's law), a "fractionation" that may result in insufficient (or excessive) current densities and low or no efficacy or adverse effects in certain sites.

An additional challenge to controlling brain state changes is that tissue anisotropy is not uniform or constant but it varies as a function of differences in cortical cytoarchitecture and of the state of activation within the volume where putative (endogenous) or exogenous (e.g., electrical stimulation) currents diffuse. These inter-regional or areal differences translate into time- and space-constant differences that make the probability of generation of action potentials and their conduction velocities behave differentially. When present, these differences lead to the spatio-temporal dispersion of endogenous or exogenous (e.g., electrical stimulation) currents and to a lower than desirable current flux through the region of interest—and thus potentially to loss of therapeutic efficacy. However, the opposite may also occur and current flux may be higher than desirable for efficacious control or safety purposes. The fact that electrical currents both trigger and control seizures depending on the stimulation parameters used, such as frequency and intensity, among many other factors, should not be ignored by those who use this modality for therapeutic purposes. In addition to the inherent widespread morphological or structural anisotropy of nervous tissue, diffusion of electrical potentials also depend on: a) the state (at both global and local levels and at long and short time scales) of the network; b) on the level (spike frequency) and pattern of spike activity and the "valence" (inhibitory or excitatory) of inputs and outputs, which are likely reflected in changes in tissue conductivity/diffusivity and responsivity to both endogenous and exogenous currents. For example, tissue resistivity is altered by bursts of epileptiform discharges of only a few seconds duration and frequent seizures often alter tissue osmolality, both of which are likely to negatively impact therapeutic efficacy, unless these factors are taken into account and measured.

As for electrical stimulation, the most investigated therapeutic modality for pharmaco-resistant epilepsies, the electric field E, at every point i on the surface of a charged needle (which closely approximates in shape the electrodes used in humans for treatment purposes) is similar to the set of diffusion limited aggregation growth probabilities and in this sense, the electric field E, is also a multi-fractal set. This means that different "regions" in the electric field (and by extension in the tissue where the field is active) are not only fractal but have different fractal values or properties at different points. That an electric field as described above is a multi-fractal set brings to the fore one of the central themes of this work, the spatio-temporal "inhomogeneity" of a therapy (electrical) and the requirement (for optimization of this treatment modality) to apply concepts (from multi-fractal theory, among others) to quantitatively characterize this complex phenomenon.

Prior art therapies also ignore the dampening and the linear and non-linear distortions of frequency, phase, harmonics and amplitude that invariably occur as currents travel through brain tissue. More specifically, prior art therapies and interventions for blocking, abating, or preventing undesirable state changes ignore tissue anisotropy, dielectric hysteresis, state and circadian influences at local and global scales and the changing nature (non-stationarity) in the type, pattern and level of neuronal activity as a function of state and time as reflected in intra-individual and inter-individual differences in seizures.

The present inventor has investigated the foregoing issues in conducting research to improve therapies available to epileptic patients. Figures presented in U.S. patent application Ser. Nos. 12/729,093 and 61/210,850 depict the power spectrum (a representative estimation of brain activity) of neuronal activity recorded over 162 hours from the same site in the same human subjects. Those figures demonstrate how the activity of the epileptogenic zone as reflected in the power spectrum changes as a function of time. A look at those spectrograms and at the temporal evolution of the values of the decimal logarithm of the standard deviation; of the generalized Hurst exponent; and of the singularity spectra width values of two seizures recorded from 11 subjects (each subject's seizures are in the same row), point clearly to the importance of tailoring therapy to intra- and inter-individual differences; it is improbable that electrical stimulation with fixed parameters (the current state-of the-art) delivered to each of these seizures will have the same effect, let alone that it will be uniformly beneficial.

The inhomogeneity/lacunarity of involvement of tissue during an undesirable event, as seen in figures presented in U.S. patent application Ser. Nos. 12/729,093 and 61/210,850, underscores the importance of quantifying and accounting for lack of uniform tissue involvement (inhomogeneity) by these abnormal events.

If seizure properties features are determined using spectral methods and classified into clusters (each cluster represents a given type of seizure) using vectors of their properties (e.g., the log of the standard deviation, the singularity spectra width values, etc.), the inventor has found that there is more than one cluster or seizure type for each subject, for seizures originating from the same site, and that the number of clusters changes in time, suggesting corresponding changes in the number of main "modes" of neural activity. The non-stationarity of seizures origin in a subject from the same brain regions is supported by recent the observation that signal spectral and other properties change throughout a seizure, a phenomenon that draws attention to the limitations (e.g., lower efficacy, more adverse events) of using the same therapy (e.g, constant parameters) throughout the course of a seizure and of not tailoring it to its spectral properties, complexity, entropy or information measures. The non-stationarity of seizures (largest around onset and termination) may reflect "start-up transients" (in a dynamical sense) and temporo-spatial dispersion of the ictal signal (which impacts the signal-to-noise ratio). These and local and global state-dependencies of certain signal features, account in part for within-seizure spectral and other fluctuations or non-stationary behavior.

Seizures may have a latent circadian periodicity which could be extracted as periodicity in the variation of the pseudo-F-statistic maximum values. This periodicity may disappear as a function of time, state and other factors. A figure presented in U.S. patent application Ser. Nos. 12/729,093 and 61/210,850 depicts the time evolution of the values of the Pseudo-F statistic (a measure of cluster tightness) of seizures recorded from the same site and from the same individual. Notice the red clouds seen at 1.2 (~12 hr) and 1.4 (~24 hr) in a log of time axis) and present from the start of the recording and indicative of a circadian tendency for seizure properties to cluster, that is, to be highly similar, vanishes after approximately 110 hours, indicating the loss of the circadian trend. This observation further exposes the variability of abnormal brain activity over intermediate time scales (tens of hours), variability that must be detected and measured to optimize (as a function of time) therapeutic efficacy.

Other important factors that are ignored by current therapies are: (i) seizure blockage does not necessarily translate into prevention of loss of cognitive functions, the most disabling seizure symptom; (ii) the inherent and inevitable delay (vide supra) in arrival of the therapy to its target site, delay which depends among others on the therapeutic modality (relatively short for electrical currents and relatively long for drugs and thermal energy); (iii) the degree (low or high) of morphological similarity among oscillations that make up a seizure, determines the probability (high if the oscillations are highly similar) of blockage especially if electrical stimulation is the therapy of choice; (iv) the lack of uniformity in flow direction and in density of both the abnormal activity and the therapy, as well the differences in their speeds of propagation, their phase-locking levels, and their degrees of regularity.

SUMMARY OF THE DISCLOSURE

In one embodiment, the present disclosure provides a method, comprising: detecting, in at least a first brain region of a patient, an electrical activity relating to an epileptic activity; determining a first regularity index of said electrical activity; and applying at least one first electrical stimulation to at least one neural target of said patient for treating said epileptic event, in response to said first regularity index being within a first range.

In one embodiment, the present disclosure provides a method, comprising: detecting a first electrical activity relating to a first epileptic activity in at least a first brain sub-region of a patient; detecting a second electrical activity relating to a second epileptic activity in at least a second brain sub-region of said patient; determining a phase-locking index between said first electrical activity and said second electrical activity; and applying at least one first electrical stimulation to at least one neural target of said patient for treating said epileptic activity, in response to said phase-locking index being inside a first range.

In one embodiment, the present disclosure provides a method, comprising: detecting a first electrical activity relating to a first epileptic activity in at least a first brain sub-region of a patient; detecting a second electrical activity relating to a second epileptic activity in at least a second brain sub-region of said patient; determining a phase-locking index between at least said first electrical activity and said second electrical activity; applying at least one first electrical stimulation to at least one neural target of said patient to modify said phase-locking index if said phase-locking index is outside a first range; and applying at least one second electrical stimulation to at least one neural target of said patient to treat said epileptic activity.

In one embodiment, the present disclosure provides a medical device system, comprising: an epileptic event detection module configured to detect an epileptic event; at least one sensor configured to collect one or more electrical activity signals from at least one region of the brain of a patient; a regularization determination module configured to determine the regularity of said electrical activity; a neuronal regularization module configured to modify a regularity index of electrical activity in said at least one brain region of said patient; a phase-locking determination module configured to determine the degree of phase-locking between said first electrical activity and said second electrical activity; a phase-locking module configured to modify a phase-locking index between a first electrical activity in said at least one brain region and a second electrical activity in a second brain region of said patient; and a stimulation module configured to apply an electrical stimulation to at least one neural target of said patient based on an indication of said epileptic event.

In one embodiment, the present disclosure provides a non-transitive, computer-readable storage device for storing instructions that, when executed by a processor, perform a method as described herein.

BRIEF DESCRIPTION OF THE DRAWING FIGURES

Figure 2:
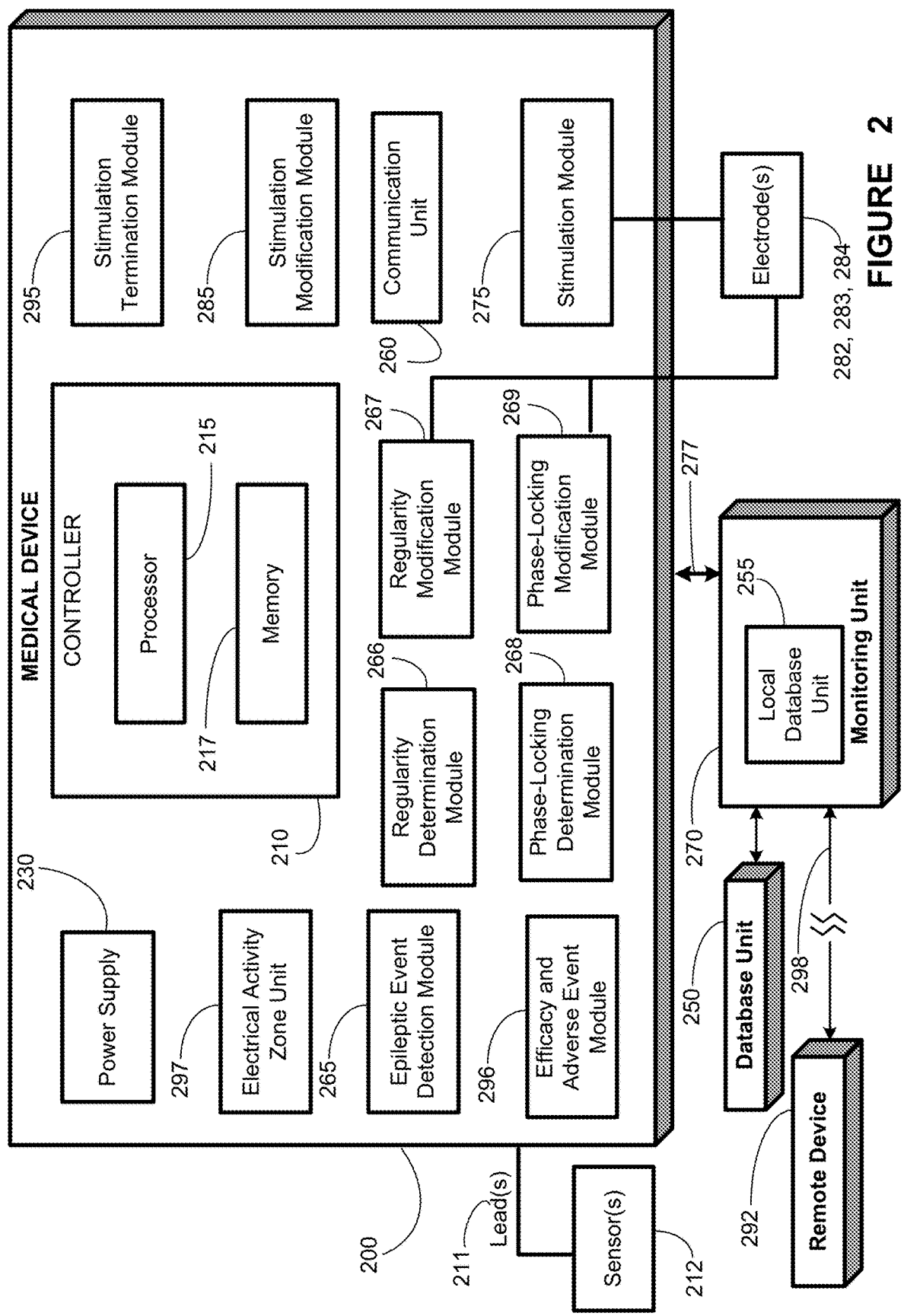

FIG. 2 presents a block diagram of a medical device system, in accordance with one illustrative embodiment of the present disclosure.

Figure 3:
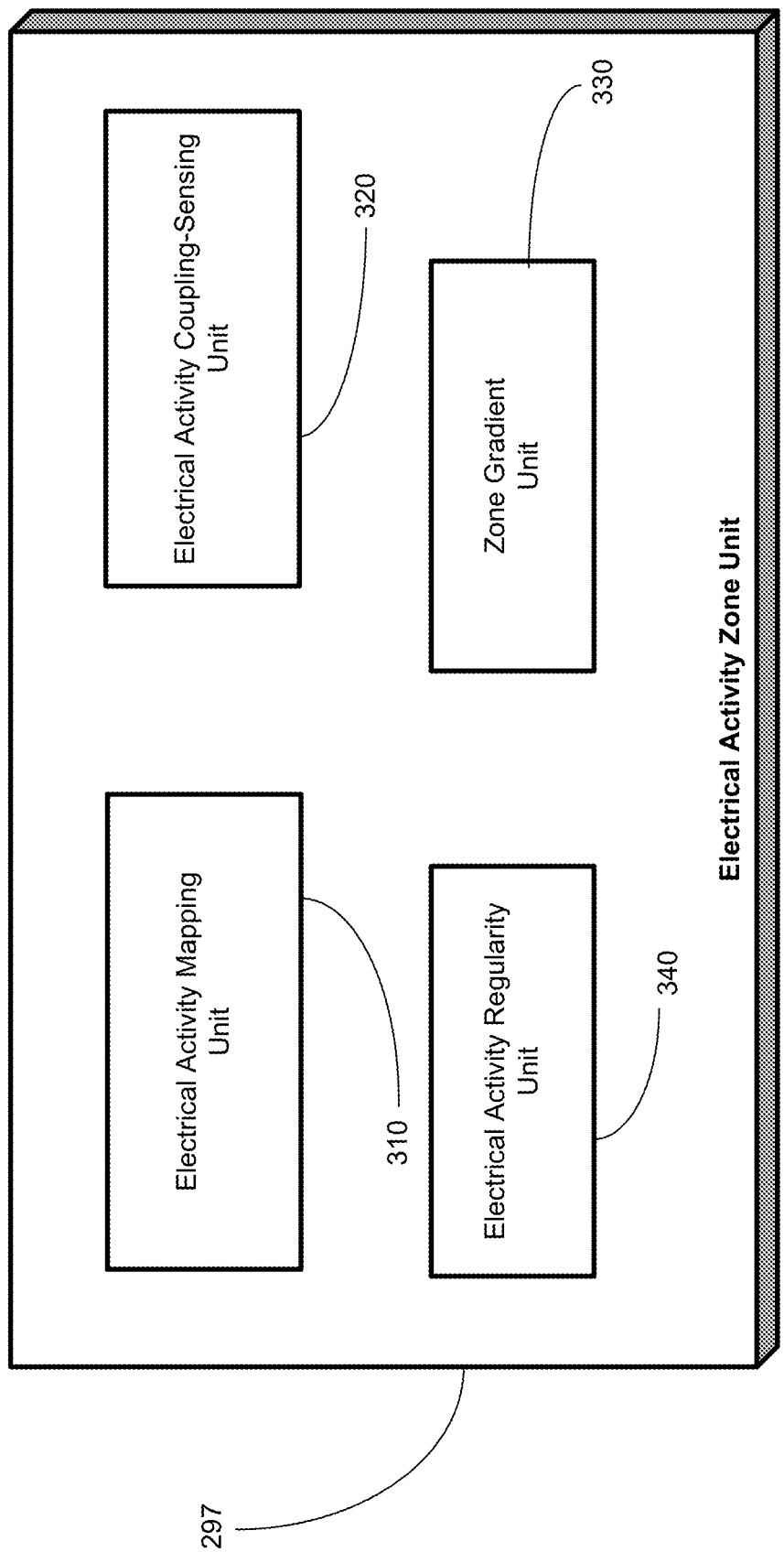

FIG. 3 presents a block diagram of an electrical activity zone unit, in accordance with one illustrative embodiment of the present disclosure.

Figure 4:
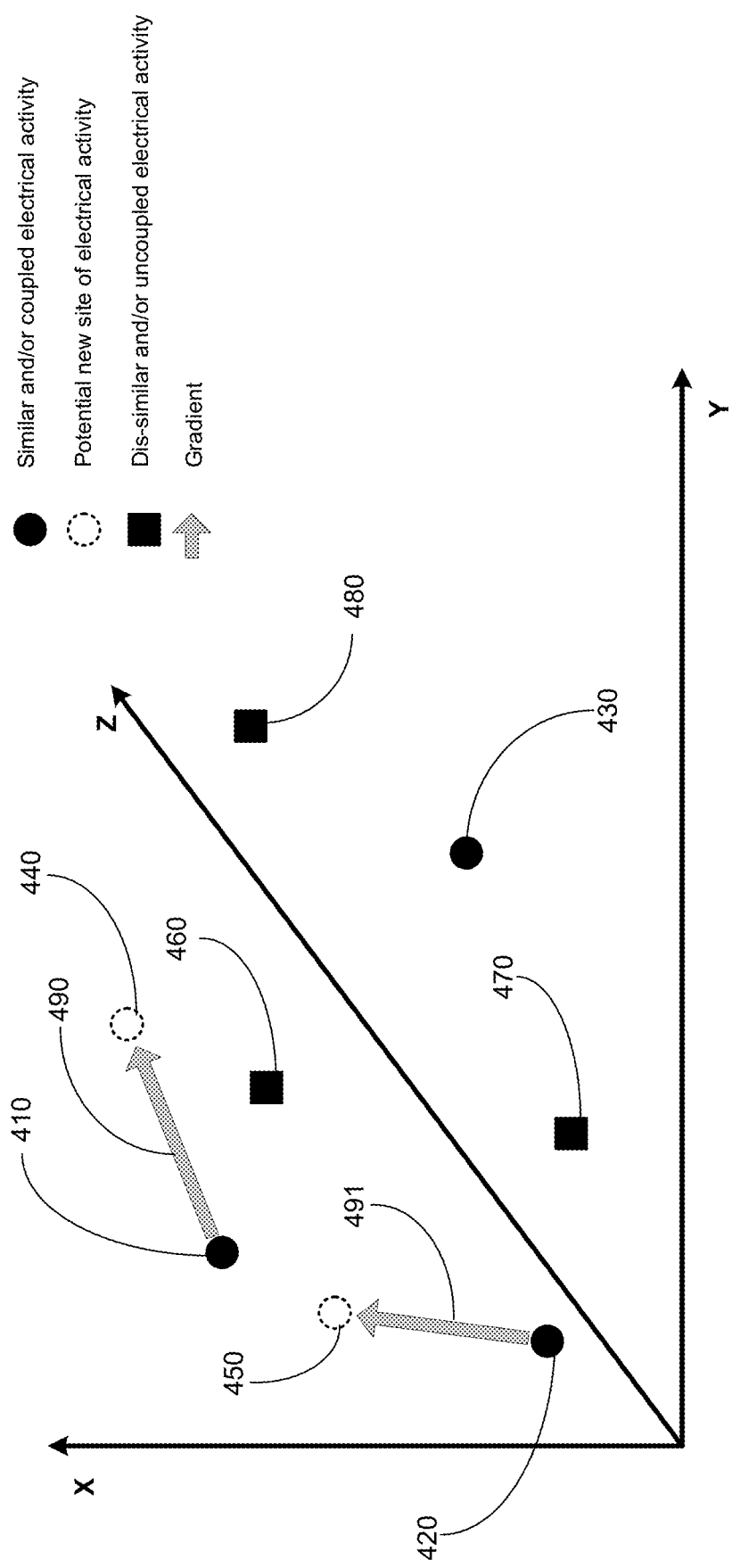

FIG. 4 depicts an exemplary mapping of a patient's brain activity, in accordance with one illustrative embodiment of the present disclosure.

Figures 5A, 5B:
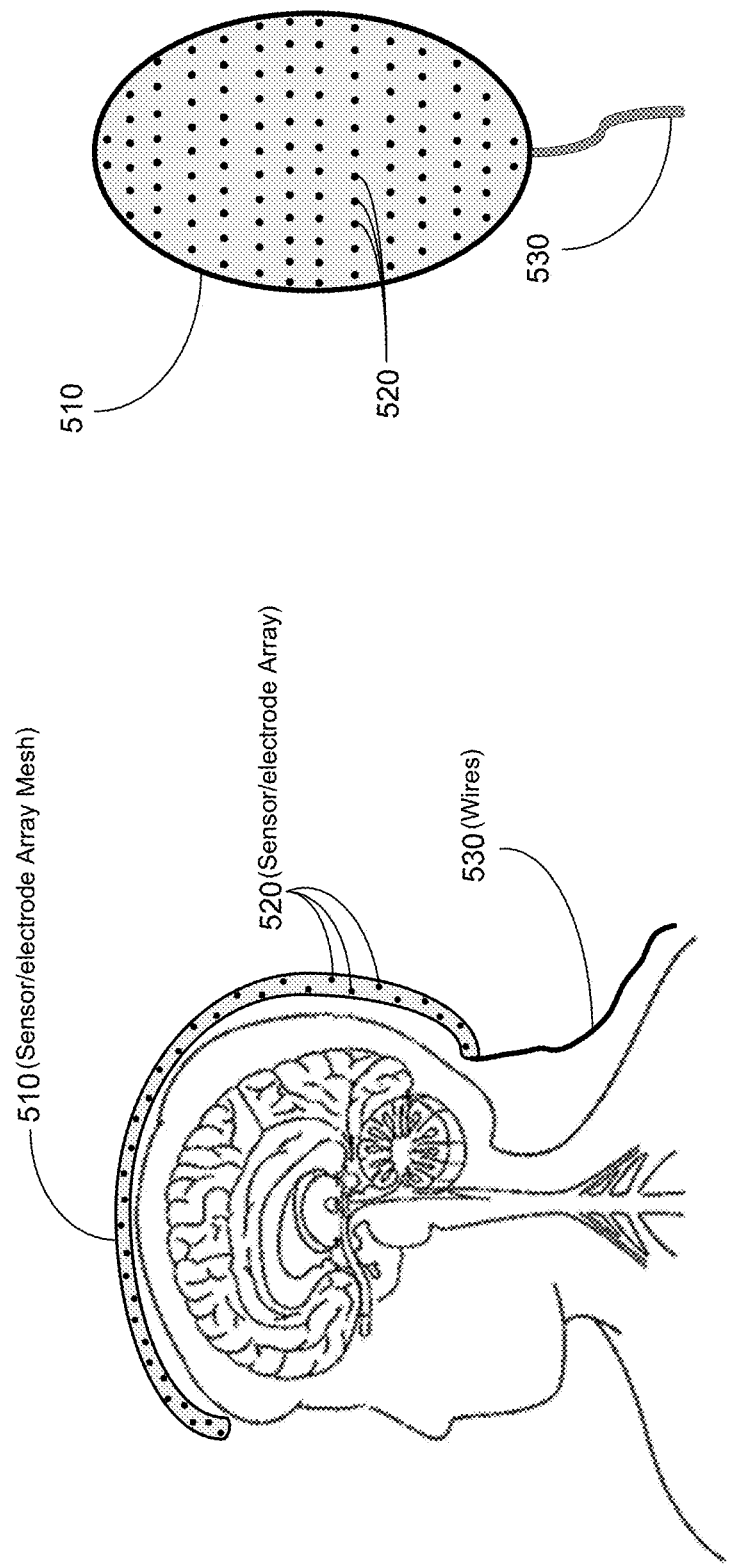

FIG. 5A depicts a sensor/electrode system, in accordance with one illustrative embodiment of the present disclosure.

FIG. 5B depicts a sensor/electrode system, in accordance with one illustrative embodiment of the present disclosure.

FIG. 6 shows a flowchart depiction of a method, in accordance with one illustrative embodiment of the present disclosure.

FIG. 7 shows a flowchart depiction of a method, in accordance with one illustrative embodiment of the present disclosure.

Figure 8:
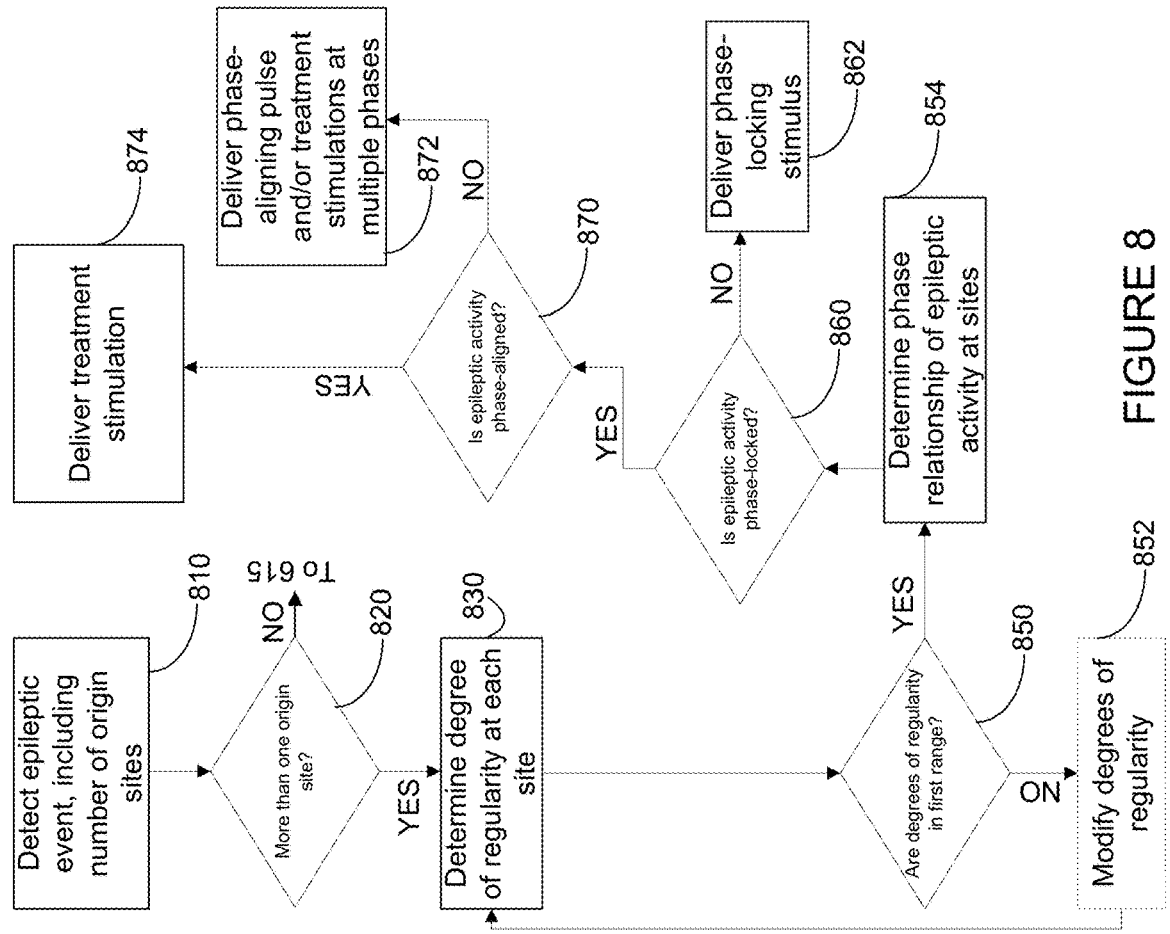

FIG. 8 shows a flowchart depiction of a method, in accordance with one illustrative embodiment of the present disclosure.

Figure 9:
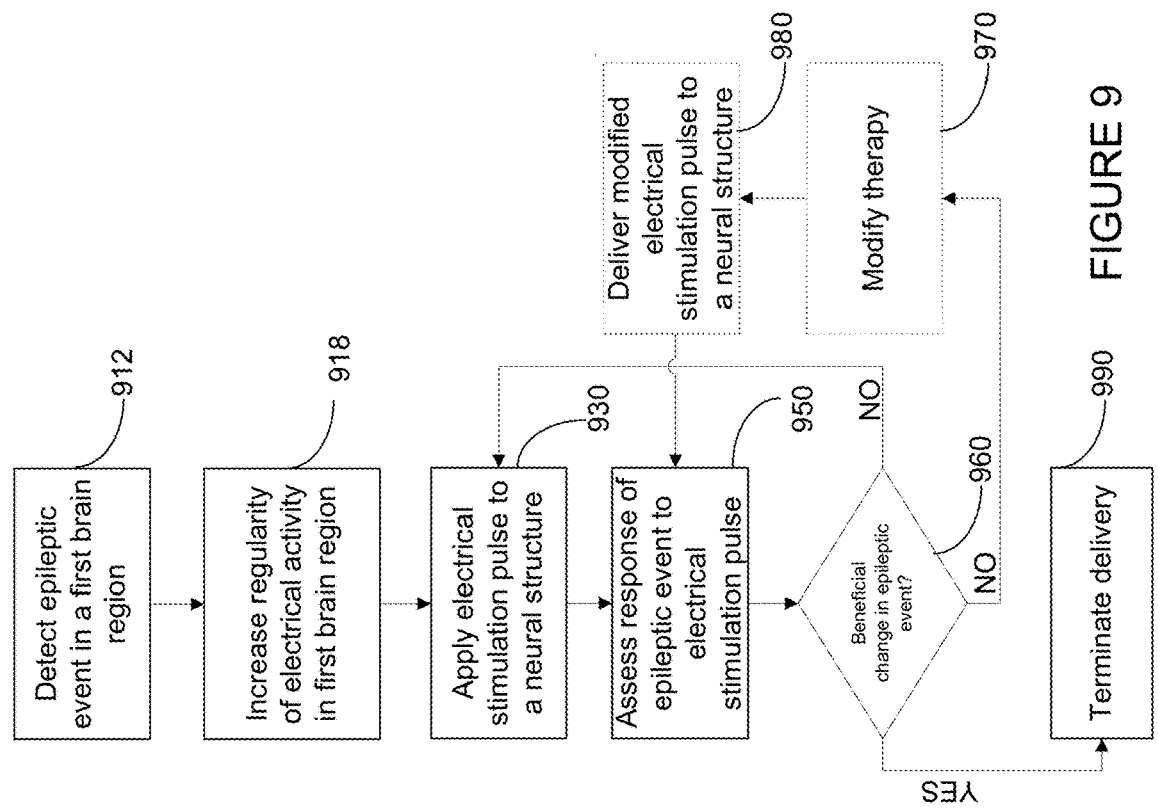

FIG. 9 shows a flowchart depiction of a method, in accordance with one illustrative embodiment of the present disclosure.

FIG. 10(a) shows electrical measurements of epileptic brain activity and the response to neurostimulation for six different seizures.

FIG. 10(b) shows electrical measurements of epileptic brain activity and the response to neurostimulation for two different seizures.

FIG. 10(c) shows an enlarged view of a portion of the response evoked by electrical pulses applied to Seizure Number 6 in FIG. 10(a).

Figure 11:
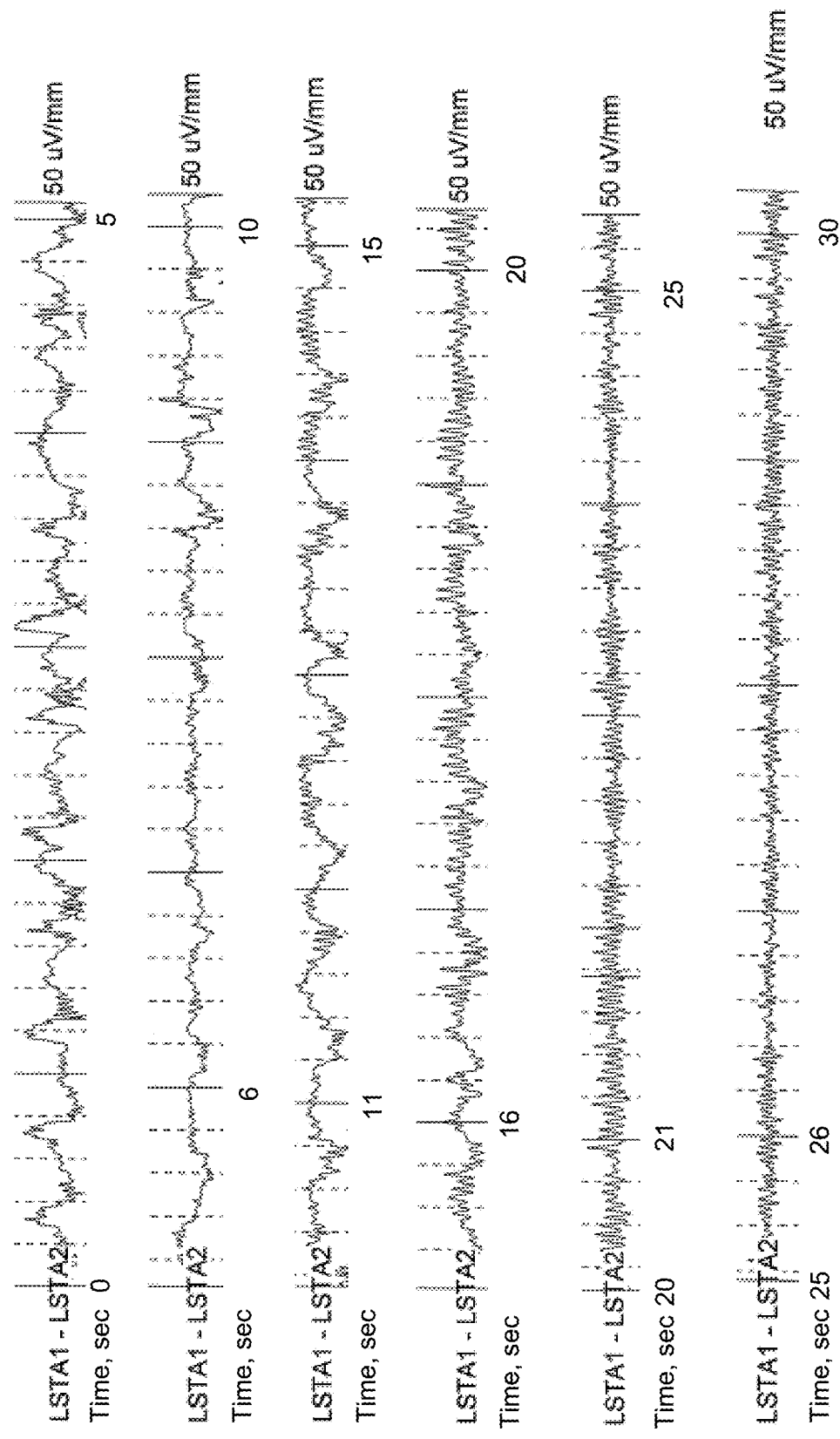

FIG. 11 shows a representative evolution of electrical activity relating to a patient's epileptic event from less regular to more regular.

Figure 12A:
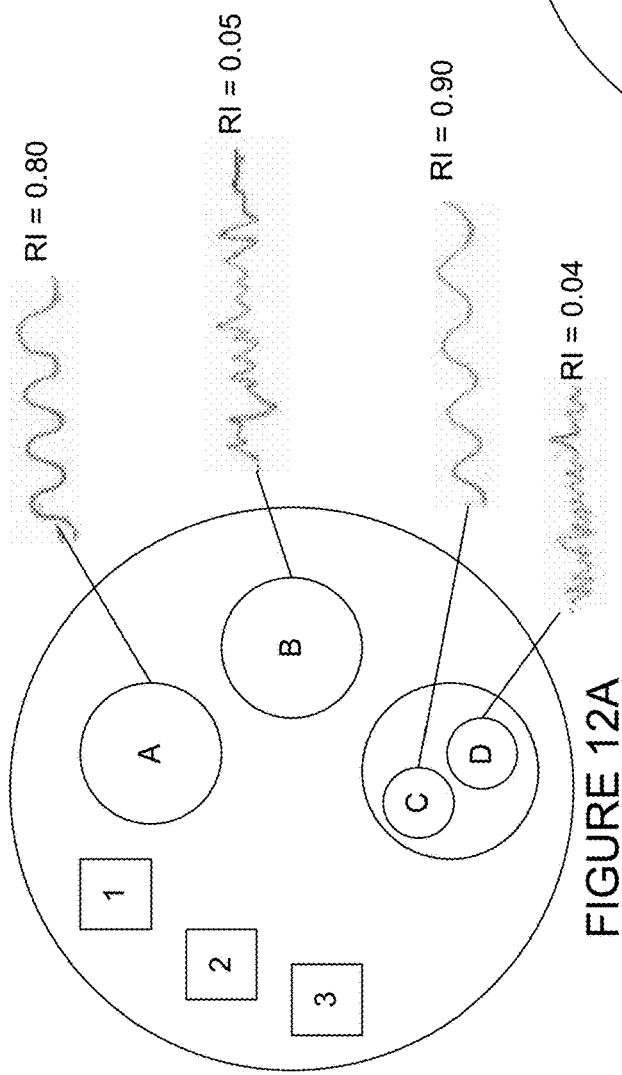

FIG. 12A shows examples of oscillations recorded from various sites that have different (high and very low) regularity index values.

Figure 12B:
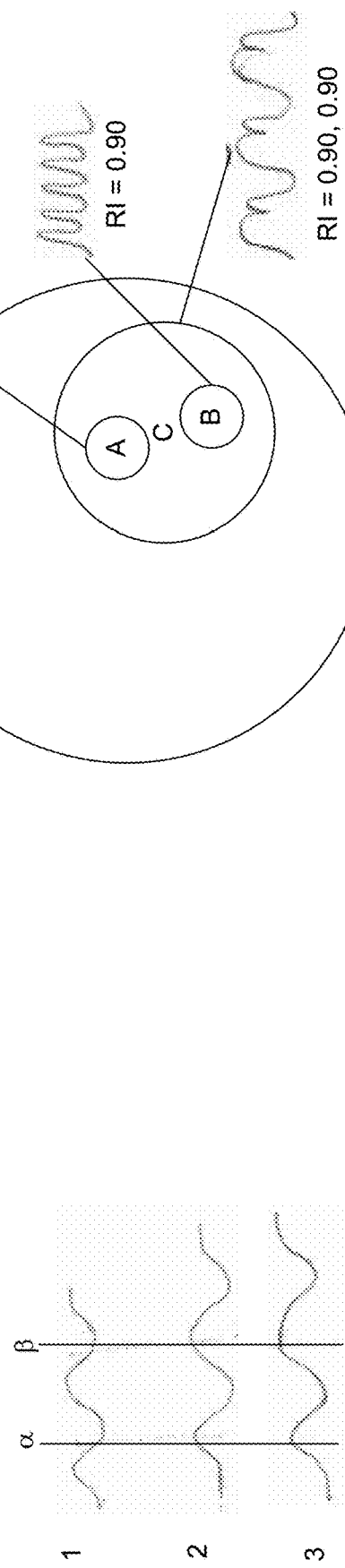

FIG. 12B shows examples of neuronal oscillations that are phase-locked but not phase aligned (1 and 2) and of oscillations that are both phase aligned and locked (2 and 3)

Figure 13:
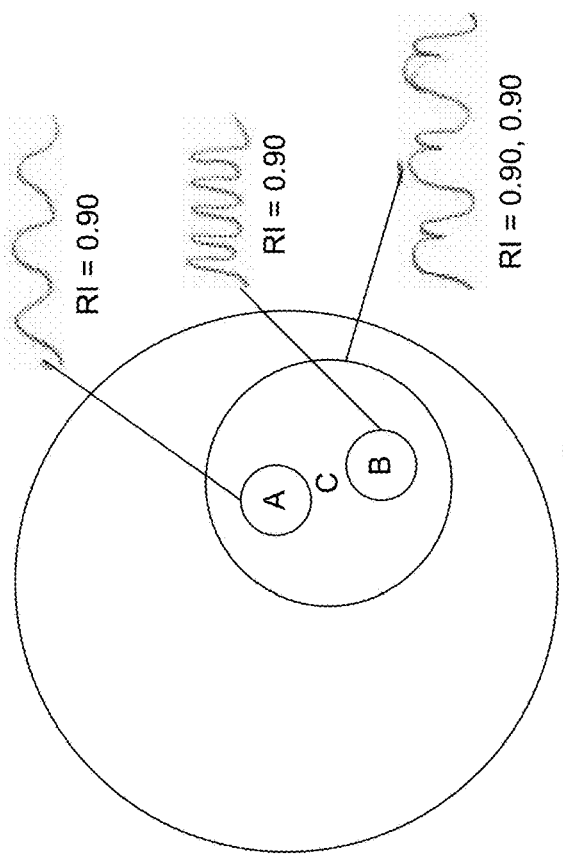

FIG. 13 depicts a neural region (C) and two sub-regions (A and B), each generating highly regular oscillations but at different frequencies.

Figure 14:
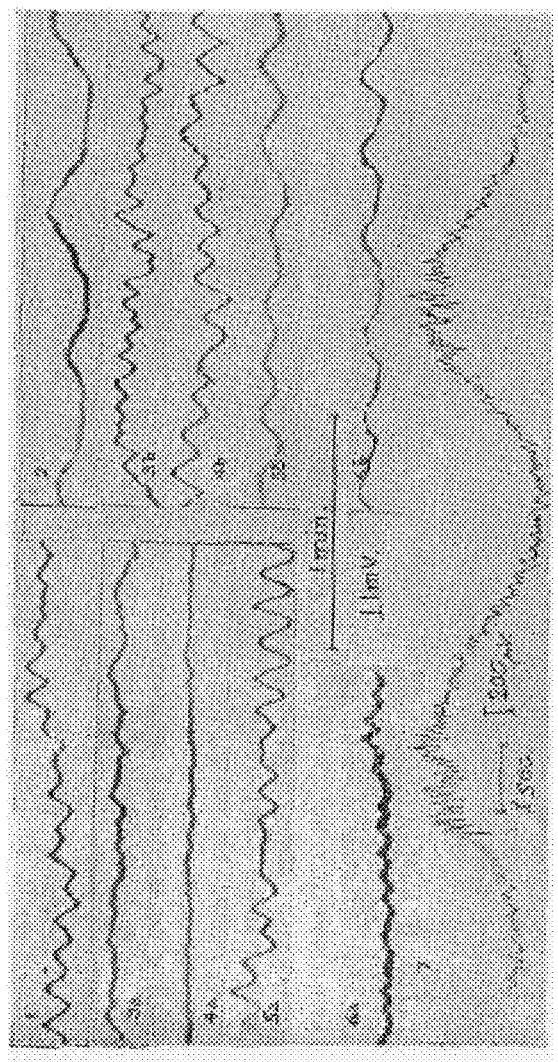

FIG. 14 depicts infra-slow rhythms of brain electrical activity.

DETAILED DESCRIPTION OF THE DISCLOSURE

The occurrence of trains of oscillations with highly similar waveforms (frequency and amplitude) within a brain region/network or between brain regions/networks may be interpreted as an indication that these oscillations are generated by highly regular and/or phase-locked generators. More detail regarding these topics can be found in U.S. patent application Ser. No. 12/729,093, incorporated herein by reference.

Embodiments of the present disclosure provide for a method, system, and apparatus for determining a regularity of neuronal activities in one or more areas of a patient's brain. The neuronal activity may relate to an epileptic event. In one embodiment of this disclosure said neuronal activity is electrical. In other embodiments, the neuronal activity may be chemical, metabolic, or mechanical. Based upon the degree of regularity, a stimulation signal, e.g., a pulse signal, may be applied to control or reduce the abnormal or undesirable electrical activity. Alternatively or in addition, the degree of regularity may be modified by a stimulation signal provided by a device.

"Regularity" refers herein to self-similarity between two or more occurrences of a cyclic phenomenon (e.g., brain or neuronal oscillations, for example, electrical oscillations). A quantified measure of regularity may be termed a "regularity index."

In one embodiment, a phase-locking index that relates to the degree of phase-locking of electrical activities corresponding to two or more brain regions or within a brain region may be determined. Based upon the phase-locking index, a stimulation signal is provided to reduce or block the abnormal electrical activity. The parameters of said electrical signal may be selected based on the level of neuronal regularity and/or phase-locking within or between regions in reference to the level of regularity and/or phase-locking that characterizes the non-seizure state oscillations. Specifically, if the regularity and/or phase-locking index drops during a seizure in reference to the non-seizure value of the index, parameters that increase said seizure regularity and/or phase-locking level may be applied to the region generating the seizure; if the regularity and/or phase-locking index increases during a seizure relative to the non-seizure value of the index, electrical signals with parameters that decrease regularity and/or phase-locking may be applied.

Figure 1A:
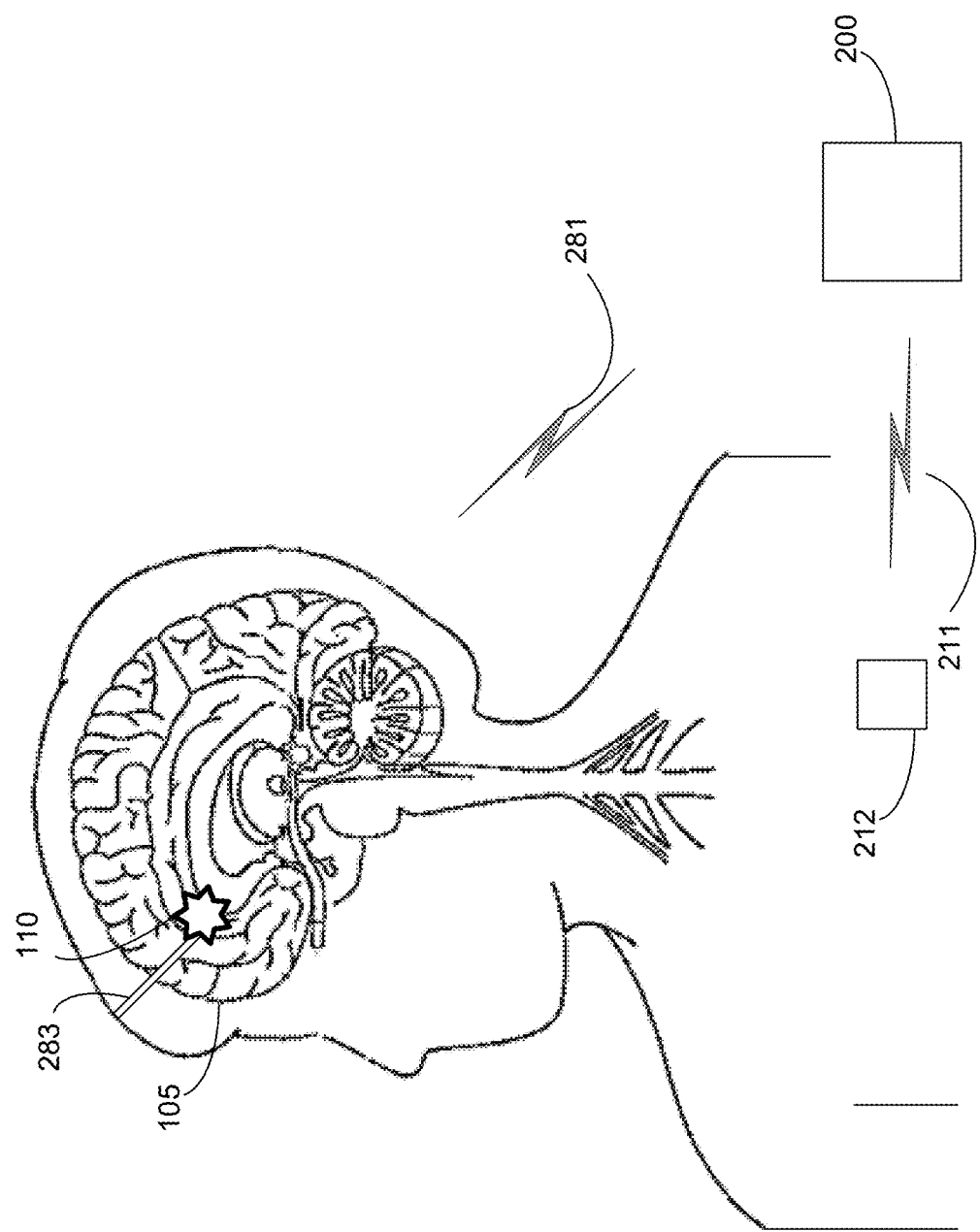
FIG. 1A depicts a medical device system, comprising an electrode implanted in the brain of a patient, in accordance with one illustrative embodiment of the present disclosure.

Turning now to FIG. 1A, a stylized medical device system is depicted. The medical device system comprises a medical device 200 and at least one sensor 212.

Figure 1B:
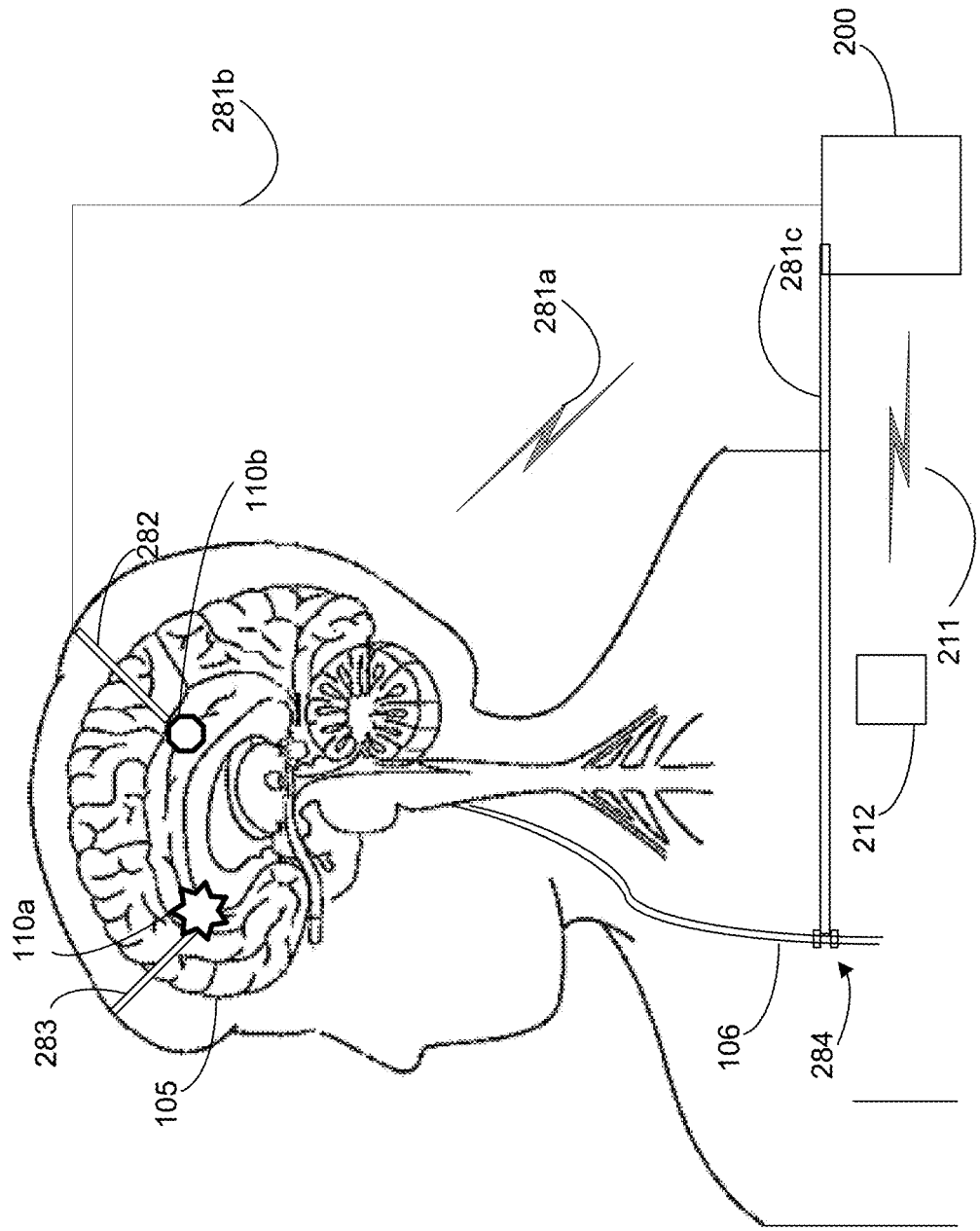
FIG. 1B depicts a medical device system, comprising a plurality of electrodes implanted in the brain or coupled to a cranial nerve of a patient, in accordance with one illustrative embodiment of the present disclosure.

In some embodiments, the medical device 200 may be implantable, while in other embodiments, such as that shown in FIG. 1B, the medical device 200 may be completely external to the body of the patient.

The sensor 212 may be implanted in the patient's body, worn external to the patient's body, or positioned in proximity to but not in contact with the patient's body. The sensor 212 may be configured to receive neurologic, autonomic, endocrine, metabolic, tissue stress marker, physical fitness/body integrity data or other data from the patient's body.

FIG. 1A depicts a medical device system comprising a medical device 200 being in wireless communication 211 with the at least one sensor 212. In other embodiments (not shown), the medical device 200 may be in communication with the at least one sensor 212 via a lead or other wired communication channel.

The medical device system shown in FIG. 1A also includes at least one neuronal regularization electrode 283. In the depicted embodiment, the neuronal regularization electrode 283 may be implanted in the patient's brain 105 such that the terminus of the electrode 283 may be in proximity to a brain region 110 which may be an epileptogenic focus (depicted by a star) of the patient. The neuronal regularization electrode 283 may be used for delivery of an electrical stimulation to increase a degree of regularity of electrical activity in the brain region 110.

Not shown in FIG. 1A is an alternative embodiment, wherein a plurality of neuronal regularization electrodes 283 may be implanted in the patient's brain 105. A plurality of neuronal regularization electrodes 283 may be implanted such that their termini may all be in proximity to a single brain region. Alternatively, the plurality of neuronal regularization electrodes 283 may be implanted such that their termini are in proximity to a plurality of brain regions. For example, if the patient has multiple epileptogenic "foci", a plurality of neuronal regularization electrodes 283 may be implanted such that each epileptogenic focus may have at least one neuronal regularization electrodes terminus in proximity thereto. Electrodes may be also implanted in brain regions that are not epileptogenic but that may be directly or indirectly connected to the epileptogenic regions.

Also, FIG. 1A depicts the medical device 200 being in wireless communication 281 with the at least one neuronal regularization electrodes 283. In other embodiments (not shown), the medical device 200 may be in communication with the at least one neuronal regularization electrodes 283 via a lead or other wired communication channel.

FIG. 1B depicts an alternative embodiment of a medical device system comprising a medical device 200. The sensor 212 and its communication with the medical device 200 have been described above with reference to FIG. 1A. Similarly, the at least one neuronal regularization electrode 283 and its communication with the medical device 200 have been described above with reference to FIG. 1A. In FIG. 1B, the depicted communication between the medical device 200 and the neuronal regularization electrode 283 is represented by a wireless communication 281a. In the embodiment depicted in FIG. 1B, the brain region which may be an epileptogenic focus (depicted by a star) of the patient is identified as brain region 110a.

FIG. 1B additionally depicts the medical device system as comprising an electrode 282. In the depicted embodiment, the electrode 282 may be implanted in the patient's brain 105 such that the terminus of the electrode 282 may be in proximity to a brain region 110b (depicted by an octagon) of the patient. The brain region 110b may be an epileptogenic focus, or it may be not an epileptogenic focus. The electrode 282 may be used for delivery of an electrical stimulation to increase a degree of regularity of electrical activity in the brain region 110b or of regions connected to it. Alternatively or in addition, the electrode 282 may be used for delivery of an electrical therapy for an epileptic event. Even if the brain region 110b is not an epileptogenic focus, delivery of an electrical stimulation therapy to brain region 110b may be efficacious against the epileptic event.

Similarly to neuronal regularization electrode(s) 283, the medical device system may comprise a plurality of electrodes 282 (not shown).

In other embodiments, not shown in FIG. 1B, a single (set of) electrode(s) 282 may be used for neuronal regularization and the delivery of therapy.

FIG. 1B also depicts the patient's vagus nerve 106, to which electrode(s) 284 is affixed. Electrode(s) 284 is shown in communication with the medical device 200 via lead 281c. Electrode(s) 284 may be used to gather signals useful in detecting an epileptic event, regularizing the activity of an epileptic event or treating an epileptic event.

FIG. 1B depicts the medical device 200 being in wired communication (e.g., a lead) 281b with the at least one electrode 282. In other embodiments (not shown), the medical device 200 may be in wireless communication with the at least one electrode 282.

In various embodiments, electrode(s) 282, 283, and/or 284 may each perform one or more of gathering signals useful in detecting an epileptic event, regularizing electrical activity relating to an epileptic event, or treating an epileptic event. An electrode 282-284 may comprise one or more contacts, and each contact may independently perform one or more of gathering signals useful in detecting an epileptic event, regularizing electrical activity relating to an epileptic event, or treating an epileptic event.

FIG. 2 presents a block diagram of a medical device system, in accordance with one illustrative embodiment of the present disclosure.

The medical device 200 may comprise a controller 210 capable of controlling various aspects of the operation of the medical device 200. The controller 210 may be capable of receiving internal data or external data, and in one embodiment, may be capable of causing a stimulation module 275 to generate and deliver an electrical signal to target tissues of the patient's body for treating a medical condition. For example, the controller 210 may receive manual instructions from an operator externally, or may cause the electrical stimulation signal to be generated and delivered based on internal calculations and programming. The controller 210 may be capable of affecting substantially all functions of the medical device 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

In other embodiments, one or more electrode(s) 282 may be adapted to be positioned in at least one neural target of a patient. The neural target may be one or more of a target area of the brain region of the patient, a target area of a cranial nerve of a patient (such as a target area of a vagus nerve of a patient), a target area of the spinal cord of a patient, a target area of a sympathetic nerve structure of the patient, a target area of a peripheral nerve of the patient, a target area of a nerve root of a patient, or a target area of skin receptors of a patient.

The medical device 200 may also comprise a power supply 230. The power supply 230 may comprise a battery, voltage regulators, capacitors, etc., to provide power for the operation of the medical device 200, including delivering a therapeutic electrical signal. The power supply 230 comprises a power source that in some embodiments may be rechargeable. In other embodiments, a non-rechargeable power source may be used. The power supply 230 provides power for the operation of the medical device 200, including electronic operations and the electrical signal generation and delivery functions. The power supply 230 may comprise a lithium/thionyl chloride cell or a lithium/carbon monofluoride (LiCFx) cell if the medical device 200 is implantable, or may comprise conventional watch or 9V batteries for external (i.e., non-implantable) embodiments. Other battery types known in the art of medical devices may also be used.

The medical device 200 may also comprise a communication unit 260 capable of facilitating communications between the medical device 200 and various devices. In particular, the communication unit 260 may be capable of providing transmission and reception of electronic signals to and from a monitoring unit 270, such as a handheld computer or PDA that can communicate with the medical device 200 wirelessly or by cable. The communication unit 260 may include hardware, software, firmware, or any combination thereof.

The medical device 200 may also comprise one or more sensor(s) 212 coupled via sensor lead(s) 211 to the medical device 200. Sensor(s) 212 are capable of collecting one or more body signals from a patient's body. Exemplary body signals include, but are not limited to, those related to autonomic activity, such as the patient's heart beat, blood pressure, and/or temperature, among others; signals related to a neurologic activity, signals related to a metabolic activity, signals related to an endocrine activity, and signals related to tissue stress markers.

In one embodiment, the sensor(s) 212 may collect electrical data relating to electrical activity from one or more regions or subregions of the human brain. The electrical activity may relate to an epileptic event in the region(s) or subregion(s). As used herein, any two or more brain region(s) and/or sub-region(s) may be physically contiguous, physically adjacent, physically non-adjacent, anatomically connected, electrically connected, or two or more thereof.

Sensor(s) 212 may be unimodal or multimodal (e.g., collect one or more of electrical, optical, chemical, pressure, thermal, acoustic, etc. signals). Their number, location, functions, and status (active or dormant) may vary according to the task at hand.

Whatever the signal type collected by the sensor(s) 212, the signal(s) may be filtered or processed prior to further use by other modules of the medical device 200, or raw signals may be used by other modules. In one embodiment, the sensor(s) 212 may be the same as electrode(s) 282, 283, and/or 284. In other embodiments, the sensor(s) 212 are separate from electrode(s) 282, 283, and/or 284; for example, the sensor(s) 212 may be placed on the patient's skin, such as over the patient's heart or elsewhere on the patient's torso. The sensor(s) 212 and accompanying leads may be considered an interface for the medical device 200 to receive at least one of autonomic data, neurologic data, metabolic data, endocrine data, stress marker data, quality of life data, physical fitness/body integrity or other data.

More information on body signals, such as cardiac signals, respiratory signals, body movement signals, skin resistance signals, responsiveness signals, and awareness signals, as well as techniques and devices for the acquisition thereof and the determination of autonomic indices, neurologic indices, metabolic indices, endocrine indices, and stress marker indices, is provided by U.S. patent application Ser. No. 12/896,525, filed Oct. 1, 2010, which is incorporated herein by reference in its entirety.

The medical device may also comprise an epileptic event detection module 265. The epileptic event detection module 265 may be configured to detect an epileptic event from any desired input suitable for doing so. For example, in one embodiment, the epileptic event detection module 265 may be configured to detect an epileptic event from brain electrical activity data, e.g., EEG data. In another exemplary embodiment, the epileptic event detection module 265 may be configured to detect an epileptic event based on the signal(s) from elsewhere (e.g., extra-cerebral) in the patient's body. These signals may, but need not, be provided by sensor(s) 212. In one particular embodiment, the epileptic event detection module 265 may be configured to detect an epileptic event based on at least one of a cardiac activity indicative of an epileptic event or a motor activity indicative of an epileptic event.

The term extra-cerebral signal(s), as used herein, denotes signals that may or may not originate from the brain but that do not require sensors or electrodes place on the head, or on/in the brain, to record them. Examples of extracerebral signals include but are not limited to cardiac, metabolic, etc. Certain neurologic signals such as kinetic or cognitive (reaction time, memory scores, etc.) are considered extracerebral (even though they originate in the brain) because they are recordable outside the head or brain, unlike EEG or ECoG as recorded with state-of the-art equipment and methods.

Epileptic events are likely to exhibit regular neuronal activity. In one embodiment, an epileptic event may be detected by determining the degree of regularity of electrical activity in a first brain region of the patient.

More information regarding detection of epileptic events from sensed body signals, and determination of severity of and body locations affected by epileptic events, can be found in U.S. patent application Ser. No. 12/756,065, filed Apr. 7, 2010; U.S. patent application Ser. No. 12/770,562, filed Apr. 29, 2010; U.S. patent application Ser. No. 12/896,525, filed Oct. 1, 2010; U.S. patent application Ser. No. 13/040,996, filed Mar. 4, 2011; U.S. patent application Ser. No. 13/091,033, filed Apr. 20, 2011; and U.S. patent application Ser. No. 13/098,262, filed Apr. 29, 2011; all of which are hereby incorporated herein by reference in their entirety.

The medical device 200 may also comprise a regularity determination module 266. The regularity determination module 266 may be configured to determine the level(s) of regularity within one or more regions or subregions of the patient's brain. The regularity determination module 266 may do so by using any available data, such as data extracted from signals gathered by sensor(s) 212, and calculating one or more of a measure of amplitude variance, a measure of frequency variance, a measure of zero-crossings interval variance, a measure of ascending and descending slope variances, a number of extrema, a polarity of extrema, a box count, a polynomial fitting to measure the error of polynomial approximation, a Lipschitz exponent of one of the foregoing, or a Holder exponent of one of the foregoing. From the calculation, the regularity determination module 266 may determine whether the degree of regularity is within a first range, such as a range suggestive that the epileptic event would be amenable to treatment as described below.

The regularity of neuronal oscillations may be determined from an autocorrelation function, a template-matching function (wherein a first occurrence of the cyclic phenomenon provides the template for matching later occurrences thereof), or the variance of amplitude, frequency, zero-crossing interval, extrema, slope, or other parameters between the two or more occurrences of the cyclic phenomenon, among others. Determining regularity from the variance of one or more parameters may be computationally more efficient, which may be desirable to preserve battery life, expedite calculation, or both. Fractal/multifractal tools may be also applied to the body signal(s) to determine their degree of regularity of their oscillations.

In one embodiment, a regularity index may be determined relatively rapidly, such as from signals collected during a window comprising from two to twenty wavelengths of a predominant oscillation of the electrical activity. Typical predominant oscillations of epileptic electrical activity have a frequency from about 8-45 Hz, from which a regularity index according to this embodiment may be determined on signals collected over from about 20 msec to 2.5 sec.

As stated elsewhere, the regularity index may be calculated based on a raw signal of the electrical activity, or on a filtered or otherwise processed signal. A filter may be selected such that the regularity index may be determined at least in part on a frequency component of the electrical activity. The frequency component may be a single frequency or a frequency band. For example, the frequency component may have a frequency or band in the range of 1-6 Hz, 8-45 Hz, 1-200 Hz, DC to 100 Hz, 100-1000 Hz, or DC to 1000 Hz.

In one embodiment, the regularity index may be determined based on a power spectral density of the electrical activity or a power level of a selected frequency component. For example, the frequency component having the highest power level may be selected such that the regularity index may be determined at least in part on it. In another embodiment, the regularity index may be determined based on a selected frequency component, independent of its power level. For example, a particular frequency or band may be known to be generally implicated in electrical activity relating to the patient's stereotypical epileptic events.

A regularity index of the electrical activity may comprise information relating to the oscillation morphology, amplitude, and frequency of the electrical activity.

The concept of regularity may be illuminated in qualitative terms by consideration of FIG. 10(a). This figure shows the effect of five cathodal monophasic (DC) pulses on six different seizures, recorded from the same site.

Prior to the application of the stimulation at time 0, the regularity of the electrical activity of seizures 1, 2, 5, and 6 is apparent. Contrariwise, the lack of regularity of the electrical activity of seizures 3 and 4 is also apparent.

FIG. 10(a) also shows quantification of regularity. A regularity index was calculated by use of an autocorrelation function from pre-stimulation data relating to all seizures. Seizures 1, 2, 5, and 6 had regularity indices from 0.72-0.91, whereas seizures 3-4 had regularity indices from 0.12-0.28.

FIGS. 10(a) and 10 (b) show a practical benefit of increasing the regularity of electrical activity in at least one brain region of a patient. Seizures 1, 2, 5, and 6, characterized by high regularity, were attenuated/blocked by electrical stimulation therapy. Seizures 3-4, characterized by low regularity, were not attenuated/blocked by electrical stimulation therapy. It should be noted that even a single cathodal monophasic pulse may abolish a highly regular seizure, while having no effect on one with low regularity.

FIG. 10(c) further illuminates the points raised above. This figure shows the impulse or evoked response to monophasic cathodal stimulation of one of the seizures shown in FIG. 10(a). The impulse responses to cathodal stimulations show subtle phase shifts (phase resetting) which are predictive of a beneficial or non-beneficial response. Using available optimization search methods, the timing of delivery of a single (or very pulses) to cause the desirable (beneficial) phase may be found for each seizure.

The medical device 200 may also comprise a regularity modification module 267. The regularity modification module 267 may be configured to deliver a neuronal regularization electrical signal to a brain region of a patient through electrode(s) 282, 283, and or 284.

The delivery of a neuronal regularization electrical signal by the regularity modification module 267 may be based on a finding by the regularity determination module 266 that the degree of regularity of the electrical activity in question is outside a first range, such as at a low level, suggestive that the epileptic event would not be amenable to treatment as described below.

Similarly to the regularity determination module 266 and regularity modification module 267 described above, the medical device 200 may also comprise a phase-locking determination module 268 and a phase-locking modification module 269. The phase-locking determination module 268 may determine a degree of phase-locking of electrical activity between two regions and/or subregions of the patient's brain, and the phase-locking modification module 269 may modify the degree of phase-locking to render the epileptic event more amenable to treatment as described below. The phase-locking modification module 269 may modify the degree of phase-locking by delivering an electrical stimulation to a neural target via one or more electrodes 282, 283, or 284.

The electrodes 282 may be configured for modifying (e.g., increasing or decreasing) the phase-locking level between subregions within a region or between brain regions of a patient, such as two neural targets. Electrodes suitable for this application are described in U.S. patent application Ser. No. 11/151,386, which is hereby incorporated herein by reference.

As stated above, in one embodiment, the medical device 200 may also comprise a stimulation module 275 capable of generating and delivering an electrical therapy delivered to one or more electrodes 282.

Therapy may be delivered to the electrode(s) 282 by the stimulation module 275 based upon instructions from the controller 210. The stimulation module 275 may comprise various circuitry, such as electrical signal generators, impedance control circuitry to control the impedance "seen" by the leads, and other circuitry that receives instructions relating to the delivery of the electrical signal to tissue. The stimulation module 275 may be capable of delivering electrical therapy over leads to the electrode(s) 282. The stimulation module 275 may be configured to apply an electrical therapy, which may comprise one or more stimulation pulses, to at least one neural target of the patient based on an indication of an epileptic event.

The electrical therapy, and/or each stimulation pulse thereof, may comprise a plurality of parameters, such as waveform, pulse width, number of pulses, inter-pulse interval, amplitude, or phase/polarity, the timing of pulse delivery in reference to the time a zero-crossing occurs, the timing of pulse delivery in reference to the time an extremum occurs, or the timing of pulse delivery in reference to a region of an ascending or descending slope of a neuronal oscillation, among others. In one embodiment, the electrical therapy has a duration of less than 1 second. In a particular embodiment, the electrical therapy has a duration less than about one-third of the wavelength of the dominant regular oscillation. The electrical activity may be particularly vulnerable to termination by the therapy when the therapy is delivered at or near the null space commonly found at the tail end of the descending slope of the waveform, near baseline, and particularly during the early portion of the interoscillation interval.

The null space or "black hole" of oscillations may be found in any of a number of ways. In one embodiment, the null space may be found by delivering an electrical pulse of adaptable duration, said pulse beginning, for example, at the peak of the oscillation or being triggered by the oscillation reaching a certain amplitude or acceleration, and continuing until the oscillation(s) is/are terminated). Upon a finding the oscillation has been terminated, delivery of the electrical pulse may be automatically ended. The pulse may be also terminated if it exceeds a pre-specified duration, if it causes an adverse (e.g., the oscillation is strengthened) or intolerable (e.g., pain) effect, or if it exceeds a safety limit.

In another embodiment, the null space may be found by delivering a series of electrical pulses, each pulse of defined duration, beginning, for example, at the peak of the oscillation waveform. The series of electrical pulses may be delivered at a frequency slightly lower than the oscillation's frequency. For example, if the oscillation is at 25 Hz, the electrical pulses may be delivered at a frequency of 24 Hz. Thus, if the first peak of the oscillation is defined to occur at time 0, the second peak of the oscillation occurs at time 40 msec, the third peak at time 80 msec, etc. If the first electrical pulse is delivered at time 0, the second electrical pulse may be delivered at time 41.667 msec (if the oscillation was not terminated by the first pulse), the third electrical pulse may be delivered at time 83.333 msec (if the oscillation was not terminated by the second pulse), etc. Future electrical pulses of the series would be delivered at increments of 1.667 msec after a peak of the oscillation. One electrical pulse in the series would eventually be delivered at a time after an oscillation peak essentially corresponding to the null space of the oscillation, and thus would be expected to terminate the oscillation, after which pulse delivery may be stopped.

Alternatively or in addition, the 24 Hz frequency need not be fixed; further pulses can be delivered at greater or lesser times after an oscillation peak. Alternatively or in addition, a 26 Hz frequency could be used, resulting in electrical pulses being delivered in increments of 1.667 msec before a peak of the oscillation. All of the particular values discussed above are solely by way of example. This disclosure envisions applicability to other frequencies and/or the use other techniques, such as dividing the search space, moving backward or forward in the search space, etc.

An epileptic event may comprise oscillations at different frequencies within one brain region and/or between multiple brain regions. Different frequencies may have different power, as that term is used in the art of power spectra. Independently, oscillations at different frequencies may have different degrees of regularity, with some being more regular and some being less.

In one embodiment, wherein an epileptic event may be detected in the brain of a patient by determining the degree of regularity of the electrical activity in a first region of the brain of the patient, treating the epileptic event may be performed by applying at least one electrical stimulation pulse to at least one neural structure of the patient for reducing the electrical activity relating to the epileptic event, in response to the degree of regularity being greater than or equal to a first threshold.

Alternatively or in addition to electrical therapy, any other therapy may be delivered to any target tissue of the subject. In one embodiment, the delivered therapy may comprise one or more of an electrical therapy, a magnetic therapy, a chemical therapy, a heating therapy, a cooling therapy, applying a positive or a negative pressure to a target tissue, an optical therapy, a cognitive therapy, a sensory therapy, or a motor therapy. The number, locations, functions, and status (active or dormant) of therapy delivery devices (e.g., electrode(s) 282, 283, or 284, among others) may vary according to the task at hand.

In a particular embodiment, and regardless of the type of therapy delivered, the stimulation module 275 may be capable of delivering pulses of energy.

In one embodiment of this disclosure, treatment of an undesirable brain state such as epileptic seizures, modification of a regularity index or of a phase locking index of epileptic oscillations, may be performed, when required, with energy pulses or "packets", an approach not found in prior art. The amplitude, duration, shape, inter-pulse interval, (polarity/phases or degree of charge balancing of the parameters for electrical pulses) of these energy "packets", may be adapted (to increase efficacy and/or decreased adverse effects) on- or off-line to the characteristics, properties or signatures of the epileptic activity under consideration. For electrical pulses, one or more of the interpulse interval, amplitude, duration, shape, polarity, degree of charge balancing, etc. may each independently vary between individual pulses and/or between sets of pulses.

These energy pulses or "packets" may be electrical (AC or DC currents), magnetic, chemical (drugs, ions, etc), mechanical (ultrasound, negative or positive pressure) or thermal (cooling or warming) may be delivered singly (e.g., only electrical) or in any possible combination (e.g., thermal and chemical, or electrical and thermal) either simultaneously or sequentially. One of the connotations of "pulse" or "packet" in this disclosure is energy "concentrated" into short time windows (e.g., milliseconds), or continuous delivery of energy over a longer time window. For seizure control or treatment, prior art relies on electrical currents delivered over time windows (e.g., 1 sec; 10 sec; 30 sec, etc) that are much longer than those that need be used in one embodiment of this disclosure. For example, treatment of seizures with electrical currents which in prior art is performed with parameters such as 5 mA; 100 Hz delivered over 1 sec., (see Osorio et al Ann Neurol, 2005) may be applied in this disclosure over a much shorter time window (e.g., 100 msec), so as to deliver the same energy but at a higher rate. Increases in rate of delivery of energy, (without exceeding the current density safety limit) may be in certain cases and under certain conditions more efficacious for seizure control than the same energy delivered at a slower rate.

In other embodiments, the same energy may be delivered as continuous lower-amplitude pulse over a longer time period. "Continuous" in this context means that, during the longer time period, the charge is never equal to zero.

Modification of regularity or of phase locking indices of neuronal oscillations at different temporal or spatial scales, a strategy to render neuronal oscillations amenable to annihilation or to control not exploited in prior art, is also facilitated through the application of energy "packets" to neural or non-neural targets.

The functions of the stimulation module 275, the regularity modification module 267, and/or the phase-locking modification module 269, may be performed by the same unit of the medical device 200.

The medical device 200 may also comprise a stimulation modification module 285. The stimulation modification module 285 may be configured to modify at least one parameter of an electrical stimulation pulse, based on an indication the therapy did not have an efficacious result. In embodiments wherein the medical device 200 may comprise a stimulation modification module 285, the stimulation module 275 may be configured to apply the modified therapy to at least one neural target.

The magnitude or intensity, duration and whenever applicable extent of spread of changes in any of the body signal indices (autonomic, neurologic, etc.) may be used to determine their severity and quantify changes (beneficial or adverse), if any, caused by a therapy such as electrical stimulation. More information regarding how efficacious results of a therapy for an epileptic event may be assessed is given in U.S. patent application Ser. No. 13/280,178.

The medical device 200 may also comprise a stimulation termination module 295. The stimulation termination module 295 may be configured to terminate a therapy, based on an indication the therapy may have an efficacious result. The stimulation termination module 295 may also be configured to terminate therapy after a safety duration constraint, e.g., after a predetermined amount of therapy has been applied without an efficacious result. The stimulation termination module 295 may also be configured to terminate therapy if an adverse effect is detected.

The medical device 200 may also comprise an efficacy and adverse event module 296. The efficacy and adverse event module 296 may determine whether or not an applied therapy had an efficacious result, an adverse result, or no result. From this information, the efficacy and adverse event module 296 may provide information used by the stimulation modification module 285, the stimulation termination module 295, or both to perform one or more of their various functions.

More detail regarding stimulation termination and efficacy and adverse event detection is given by U.S. patent application Ser. No. 13/280,178.

The medical device system of FIG. 2 may also comprise a monitoring unit 270, which may be a device that may be capable of transmitting and receiving data to and from the medical device 200. In one embodiment, the monitoring unit 270 may be a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less interactive communication with the medical device 200 than another monitoring unit 270 controlled by a healthcare provider. Whether controlled by the patient or by a healthcare provider, the monitoring unit 270 may be a computer, preferably a handheld computer or PDA, but may alternatively comprise any other device that may be capable of electronic communications and programming, e.g., hand-held computer system, a desktop computer system, a laptop computer system, a server, a personal digital assistant (PDA), a cellular telephone, etc. The monitoring unit 270 may download operational data and program software into the medical device 200 for programming the operation of the medical device, and may also receive and upload various status conditions and other data from the medical device 200. Communications between the monitoring unit 270 and the communication unit 260 in the medical device 200 may occur via a wireless or other type of communication, represented generally by line 277 in FIG. 2.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. These data may comprise patient parameter data acquired from a patient's body, therapy parameter data, seizure severity data, and/or therapeutic efficacy data. The database unit 250 and/or the local database unit 255 may comprise (contain?) data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting references for one or more detection parameters) using the monitoring unit 270, which may include obtaining and/or analyzing data from the medical device 200 and/or data from the database unit 250 and/or the local database unit 255. The database unit 250 and/or the local database unit 255 may store various patient data.

One or more of the blocks illustrated in the block diagram of the medical device 200 in FIG. 2 may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Turning now to FIG. 3, a stylized block diagram depiction of an electrical activity zone unit 297 in accordance with one embodiment of the present disclosure is illustrated. The electrical activity zone unit 297 may comprise an electrical activity mapping unit 310, an electrical activity coupling/sensing unit 320, a zone gradient unit 330, and an electrical activity regularity unit 340. The electrical activity zone unit 297 may be capable of determining coupled electrical activity and determining zones or areas of electrical activity (e.g., seizure activity) in a patient's brain. The electrical activity zone unit 297 may be capable of determining if at least one zone of electrical activity in the brain may be correlated or coupled at least partially to at least one other zone of electrical activity.

The electrical activity mapping unit 310 may be capable of mapping (e.g., "localizing") the sites(s) of origin of various electrical activities in a patient's brain. The mapping may be based upon prior data, reference data, and/or real time or near real time data. In one example, the electrical activity mapping unit 310 may generate a three-dimensional mapping of a patient's brain as exemplified in FIG. 4 (described in further detail below). Generally, various types of electrical activity taking place in a patient's brain may be mapped. Referring simultaneously to FIGS. 3 and 4, FIG. 4 illustrates a stylized depiction of a three-dimensional mapping of electrical activity in a patient's brain. The electrical activity coupling/sensing unit 320 may be capable of determining one or more relationships between one or more detected electrical activities. For example, based upon data relating to the electrical activity, two or more electrical activities may be correlated if a determination may be made that those two instances of electrical activities are coupled (e.g., phase-locked) in some fashion or degree. This coupling may include a variety of relationships between electrical activities, such as a first electrical activity initiating a second electrical activity. Other types of relationship may include physiological similarities between the electrical activities, etc.

The zone gradient unit 330 may determine any gradient associated with any detected electric activity. As such, spread of electrical activity may be mapped/tracked or predicted based upon an expected gradient and/or an observed or actual gradient. The zone gradient unit 330 may use data from the electrical activity mapping unit 310 and/or the electrical activity unit coupling/sensing unit 320 to determine a gradient or a potential gradient between brain regions. As exemplified in FIG. 4, the various mapping, coupling and gradient information may be plotted on a three-dimensional graph representing a patient's brain and/or regions and/or subregions thereof.

The electrical activity regularity unit 340 may be capable of regularizing electrical activity in at least one region or subregion of the patient's brain. Based upon information from the electrical activity mapping unit 310 and/or the zone gradient unit 330, the electrical activity regularity unit 340 may determine that the un-coupled or unrelated electrical activities in a patient's brain may be regularized before applying a stimulation signal to attenuate or block the activity. Based upon one or more characteristics of the electrical activities, the electrical activity regularity unit 340 may determine one or more parameters of a signal that may be used to regularize at least one electrical activity in the patient's brain and/or a region and/or subregion thereof. The degree of regularity may be based upon one or more of a measure of amplitude variance, a measure of frequency variance, a measure of zero-crossings interval variance, a measure of ascending and descending slope variances, a number of extrema, a polarity of extrema, a box counting method, a polynomial fitting to measure the error of polynomial approximation, a Lipschitz exponent of one of the foregoing, or a Holder exponent of one of the foregoing.

Alternatively or in addition, an unsupervised correlation-based clustering method may be applied (with appropriate modifications as required by this disclosure) to cortical signals to determine their degree of regularity (J Neurosci Methods. 2009; 178:228-36). Subsequently, a medical device 200 may deliver an electrical signal, e.g., a pulse signal, to attenuate or entirely diminish two or more of the electrical activities. In this manner, for example, two or more seizure activities in a patient's brain may be attenuated, even though the seizure activities were substantially de-coupled at seizure onset. The electrical activity regularity unit 340 may utilize look-up features and/or calculate features to determine the potential for regularizing at least two areas of electrical activity, and attenuate the electrical activities based upon regularizing them.

Nonlinear delayed feedback stimulation (Biol Cybern 2006; 95:69-85; Phys Rev Lett 2005; 94164102; Phys Rev E Stat Nonlin Soft Matter Phys 2010; 82(2 Pt 2):026204) robust against variations of system parameters representing an intermixture of activities recorded from the regions of interests using macro-electrodes may be used for signal modification or treatment purposes. Phase model analysis combined with calculus of variation may be used to derive a waveform with which to entrain neuronal oscillations. Optimal waveforms are calculated from the phase response curve and a solution to a balancing condition.

In other embodiments (not shown), the medical device 200 may alternatively or in addition comprise a chemical activity zone unit, a thermal activity zone unit, or a mechanical activity zone unit, among others, having internal units similar to the electrical activity mapping unit 310, electrical activity coupling-sensing unit 320, zone gradient unit 330, and/or electrical activity regularity unit 340.

Turning now to FIG. 4, a graphical depiction of a mapping of electrical activity in a patient's brain, in accordance with one embodiment of the present disclosure, is illustrated. The mapping of electrical activity locations 410, 420, and 430 depict electrical activity that are likely to be coupled or related to each other. For example, the electrical activity locations 410, 420 and 430 (represented by filled-in circles) may be seizures in brain regions and/or subregions that are related/coupled to each other as a result of spread from or entrainment by one region to another. The electrical activity areas 460, 470 and 480 (represented by filled-in squares) depict areas of electrical activity that are likely not coupled or are independent of each other. These electrical activity areas may be mapped by the electrical activity zone unit 297 in one embodiment.

Moreover, in addition to determining an actual gradient relating to electrical activities, the electrical activity zone unit 297 may be also capable of determining a potential gradient relating to one or more electrical activity locations. For example, a first gradient 490 from the electrical activity 410 and a second gradient 491 from the electrical activity 420 may be identified by the electrical activity zone unit 297. Based upon an analysis of the gradient, the electrical activity zone unit 297 may be capable of determining a potential new site of electrical activity (450, 440) as depicted by the un-filled, dotted circle in FIG. 4. The gradients 490, 491 may be determined in order to determine potential future new electrical activity areas that would be coupled with or related to the detected electrical activities 410, 420, and/or 430.

The medical device 200 may utilize the electrical activity mapping information depicted in FIG. 4 to treat electrical activity area, avoid unnecessary treatment of dissimilar or unrelated electrical activity regions, and/or target potential new electrical activity areas for treatment. In this manner, the existing electrical activity, such as epileptic events, may be treated by targeting specific areas of the brain. Further potential new areas of seizure activities may be treated such that the possibility of seizure activity may be diminished.

The targeting of particular areas of abnormal or undesirable electrical activity and/or potentially abnormal or undesirable electrical activity may be made for treatment in a number of ways that would be known to those skilled in the art having benefit of the present disclosure. FIGS. 5A and 5B illustrate one such example. Turning now to FIGS. 5A and 5B, a stylized depiction of a sensor/electrode array mesh 510, in accordance with one embodiment of the present disclosure, is illustrated. FIG. 5A depicts a sensor/electrode array 520 that may be embedded or integrated into the array mesh 510. The sensor/electrode array mesh 510 is depicted as a mesh-type unit for illustration purposes only and those skilled in the art would be able to implement a variety of types of sensor/electrode arrays and remain within the spirit and scope of the present disclosure. The array mesh 510 may comprise a plurality of sensors and/or electrodes positioned in any number of configurations, such as a row-column array.

FIG. 5B illustrates a top view of the array mesh 510, in accordance with one embodiment of the present disclosure. The array mesh 510 may be formed such that a predetermined arrangement of sensors and electrodes are configured in a manner such that various portions of the brain may be targeted for treatment/stimulation. The sensors/electrodes array 520 may include positioning the sensors and electrodes such that they contact with various portions of a person's skull, targeting specific locations in the brain. Alternatively, the sensors/electrodes array 520 may include sensor and electrode elements that are capable of effectuating dermal or subcutaneous contact. The arrays may be interconnected electrically via wires 530 that may be coupled to an external device that can provide control signals and/or power for controlling the operations of the sensor/electrode array mesh 510. In this manner, the various mapped locations of electrical activity and/or potential electrical activity described in the context of FIG. 4, may be targeted for treatment. Data from the electrical activity zone unit 297 may be sent to a processing unit within a medical device to control the activation of various sensors and/or electrodes in the sensor/electrode array mesh 510, thereby being capable of providing targeted treatment for regularizing and diminishing electrical activity and/or reducing the possibility of the occurrence of electrical activity in a patient's body.

The one or more of the sensors/electrodes of sensors/electrodes array 520 may be used for sensing, modification of regularity or phase-locking indices, and/or for delivery of a therapy. Electrodes suitable for this application include, but are not limited to, those described in U.S. patent application Ser. No. 11/151,386. Other electrodes suitable for this application include, but are not limited to, scalp electrodes or brain implanted electrodes, such as depth electrodes or ECoG electrodes.

FIG. 6 shows a flowchart depiction of a method, in accordance with one illustrative embodiment of the present disclosure. In the depicted method, an epileptic event may be detected at 610. In one exemplary embodiment, detecting the epileptic event may comprise detecting at least one of a cardiac activity indicative of an epileptic event or a body movement indicative of an epileptic event. In another exemplary embodiment, detecting the epileptic event may comprise detecting an electrical activity indicative of an epileptic event in a brain region of a patient.

After the detecting at 610, a degree of regularity, such as a regularity index, of electrical activity may be determined in a first brain region of a patient at 615. The degree of regularity may be determined from an autocorrelation function, a template-matching function, a variance analysis, fractal analysis, a Hurst exponent estimation, etc. In an exemplary embodiment, the degree of regularity may be determined based on at least one of a measure of autocorrelation, a measure of amplitude variance, a measure of frequency variance, a measure of zero-crossings interval variance, a measure of ascending and descending slope variances, a number of extrema, a polarity of extrema, a polynomial fitting to measure the error of polynomial approximation, a box counting method, a Lipschitz exponent of one of the foregoing, a Holder exponent of one of the foregoing, or two or more thereof.

Thereafter, a determination may be made at 620 whether the degree of regularity is inside a first range. The value of the range may be set to any range of values found to be effective in this method. In a particular embodiment, the degree of regularity is determined from a regularity index having a set of possible values of 0.0-1.0, and the first range may have as a lower bound any value from 0.3 to 0.7, such as 0.3, 0.35, 0.4, 0.45, 0.5, 0.55, 0.6, 0.65, or 0.7, among others, and may have as an upper bound any value from 0.6 to 1.0, such as 0.6, 0.65, 0.7, 0.75, 0.8, 0.85, 0.9, 0.95, or 1.0, provided the selected upper bound is greater than the selected lower bound.

In one particular embodiment, wherein the regularity index is determined from an autocorrelation function, the first range is 0.6-1.0

If the degree of regularity is greater than or equal to the first threshold, at least one electrical stimulation may be applied to at least one neural target of the patient for treating the epileptic event, at 630.

The electrical stimulation may be applied at any time during the epileptic event. In one embodiment, the electrical stimulation may be applied at a downslope, zero crossing of at least one neuronal activity oscillation of the brain of said patient.

In an exemplary embodiment, the electrical stimulation may comprise one or more electrical stimulation pulses. The electrical stimulation may be considered an electrical signal. An electrical stimulation, electrical stimulation pulses, and an electrical signal may have a number of parameters discussed above. In one embodiment, an electrical signal may have a programmed on-time. In one embodiment, an electrical pulse may have a programmed pulse width.

The neural target to which therapy may be applied may be at least one of the patient's brain, a target portion of the patient's brain, a cranial nerve of the patient, or a target portion of the cranial nerve of the patient. In one embodiment, an electrical therapy may be applied to a first target area in at least one of a brain region or a cranial nerve of the patient.

Control of seizures as taught in prior art, is through delivery of electrical currents at a single frequency (e.g., 100 Hz.), an approach that may be efficacious if seizures' oscillations are highly regular and/or phase-locked/aligned. Unlike prior art, this disclosure takes into account the importance of these factors (regularity and/or phase locking/alignment) in determining the probability of therapeutic efficacy and therefore includes them in treatment algorithms.

Modification of the regularity or of the phase locking indices of neuronal oscillations through entrainment or phase resetting, may be performed using known techniques or methods. In one embodiment of this disclosure, entrainment may be achieved by applying simultaneously energy "packets" at several frequencies. For example, electrical currents may be delivered as sine waves at 0.001 Hz upon which sine waves at lower frequencies (e.g., [0.00001, 0001, 0.001 Hz, 0.1 Hz, 1 Hz, 10 Hz, 100 Hz, 1000 Hz) are superimposed to create a "fractal" energy pulse. The fractal may be pure or statistical. Entrainment of neuronal physiologic or pathologic neuronal oscillations may be easier to achieve if the frequency of the entraining oscillations is similar or has a certain harmonic relation to the frequency of the oscillations to be entrained. That is, the success of entrainment may be dependent on the state of the brain and on the spatial scale at which it should be achieved. Entrainment during slow wave sleep, a state during which oscillations in the delta band (e.g., 1-3 Hz) are predominant, is more likely to occur if the entraining oscillations' frequency band is delta. "Steady" (in reality they change very slowly) differences in potential may be recorded between cortical regions, differences that bear a certain correlation with faster neuronal oscillations as recorded with the EEG or ECoG using conventional (e.g., 1-70 Hz) filter settings. Prior art aimed at seizure control overlooks these "steady" cortical potential differences known as "infra-slow" (0.5-2 cycles/min; 1-1.5 cycles/min) oscillations, which bias the behavior (excitability level) of neurons in the region over which they spread or of distant regions connected to that over which they spread.

FIG. 14 depicts infra-slow rhythms of brain electrical activity (Nature 1957; 179: 957-59). Trace 1: motor cortex, 8 min$^{-1}$. Trace 2: striate cortex, 1-7 min$^{-1}$. Traces 3a and 3b: before and after strychnine poisoning. Traces 4a and 4b: before and after prolonged irritation of the hypothalamus. Traces 5a and 5b: before and two hours after injection of luminal. Trace 6a: sensory cortex (superficial). Trace 6b: sensory cortex (1-2 mm depth). Trace 7: Trace 1 with increased speed and amplification.

By way of example, the role of infra-slow or of slow oscillation on the emergence of fast cortical oscillations ("spindles") as shown in FIG. 14, Trace 7, is temporally restricted to the rising phase of the infra-slow oscillations (FIG. 14, Traces 1-2) and more specifically when this phase is negative in the frontal relative to the posterior regions.

While FIG. 14 does not contain examples of epileptic activity, it is shown here to emphasize the role that slow (about 0.1-3 Hz) and infra-slow oscillations (less than about 0.1 Hz) play on determining brain excitability and the emergence of the fast frequencies (e.g., beta and gamma waves, about 14-45 Hz) that characterize seizures as recorded using conventional (e.g., 1-70 Hz) filter settings. The role of slow and infra-slow oscillations in conventional EEG/ECoG settings are usually ignored because of the filter settings applied to them. Conventional EEG/ECoG filter settings remove much information outside of 1-70 Hz. Typically, unless they reach a certain amplitude, oscillations between 0.1 Hz and 1 Hz may be unrecordable with a 1 Hz low frequency filter. Thus, primarily only the fast frequencies are seen and slow and infraslow oscillations are filtered out. The fast frequencies often "ride" on slow or infra-slow waves that are not visible due to the filter (e.g., 1 Hz) applied to the signal.

The probability of having similar values in regularity and phase locking/alignment in a given regions or regions, is a function of degree of coupling (anatomical, electrical or chemical) within or between said regions, being higher for regions highly coupled than for regions that are weakly coupled or uncoupled. Coupling between regions may change as electrical or chemical changes spread across the neuropil; those mediated by infra-slow or slow oscillations encompass larger regions that those mediated by faster frequency oscillations.

Similar considerations apply to even slower oscillations, such as those on ultradian, circadian, and menstrual timescales.

If the degree of regularity is determined at 620 to be outside the first range, then the degree of regularity of the electrical activity may be modified at 640. The degree of regularity may be modified by delivery of a neuronal regularization electrical stimulation to the first brain region, at least one second brain region connected to the first brain region, or both. The neuronal regularization electrical stimulation may comprise at least one entraining pulse. The neuronal regularization electrical stimulation may comprise one electrical stimulation pulse or a plurality of electrical stimulation pulses. Drug pulses, thermal pulses, or other techniques may be used to modify the degree of regularity of a brain region(s)' oscillations.

Those skilled in the art appreciate that modification and/or abatement of undesirable cortical oscillations may be performed non-invasively (e.g., from the scalp) by delivering transcranial electrical stimulation/currents or magnetic stimulation to a neural or non-neural target, for the purpose of exerting a beneficial effect either directly to said region or indirectly to regions connected to said target, effects that may outlast the duration of current delivery.

The parameters of the neuronal regularization electrical stimulation may be determined by a physician during workup of the patient, or may be found by traversing the search space during performance of the method. For example, during the first loop through 640, the electrical activity may have a first degree of regularity $R_1$. A first neuronal regularization electrical stimulation may then be delivered to effect a change at 640. Upon return of flow to element 620 via element 615, the electrical activity may have a second degree of regularity $R_2$. If $R_2$ is outside the first range but is closer to the nearest bound of the first range than was $R_1$, the properties of the first neuronal regularization electrical stimulation may be considered to have improved the degree of regularity and may be used as a basis for establishing the properties of a second neuronal regularization electrical stimulation. If $R_2$ is outside the first range and further from the nearest bound of the first range than was $R_1$, the properties of the first neuronal regularization electrical stimulation may be considered to have impaired the degree of regularity, and other properties may be used as a basis for establishing the properties of a second neuronal regularization electrical stimulation.

The modification at 640 is optional. In other embodiments, if the degree of regularity is outside the first range, flow may return to determining the degree of regularity at 615. The degree of regularity of an electrical activity is likely to change over the course of an epileptic event. For example, FIG. 11 shows ECoG seizure data collected from a patient with epilepsy using electrodes located at a left subtemporal anterior (LSTA) position over 30 sec of a seizure suffered by the patient. As can be seen, the EEG data varied from qualitatively less regular (e.g., at 0 to 5 sec) to qualitatively more regular (e.g., at 20 to 30 sec) over the course of said epileptic event. The present inventor has also observed data varying from qualitatively more regular to qualitatively less regular during epileptic events.

Periodic determination of the degree of regularity at 615, such as at a rate of at least 4 times per second, followed by the determination at 620, may eventually reveal a degree of regularity inside the first range in the absence of any modification at 640.

In another embodiment, if the degree of regularity of the electrical activity in the first brain region is outside of the first range, another regularity index or other measure of regularity may be determined for another electrical activity in a sub-region of the first brain region. It may be that the other electrical activity has another regularity index inside a second range (which may have the same bounds as the first range, or may have different bounds), wherein such regular electrical activity in the sub-region is sufficient to make applying at 630 likely to be efficacious in treating the epileptic event. If the other electrical activity has another regularity index outside the second range, a modifying stimulation, such as an electrical stimulation, may be delivered to a neural target to make the other electrical activity more regular and the epileptic event more amenable to efficacious therapy.

For example, under certain conditions, highly regular (e.g., regularity index=0.85) neuronal oscillations may be an "intermixture" or "admixture" of highly regular oscillations with different frequencies. FIG. 13 depicts a neural region (C) and two sub-regions (A and B), each generating highly regular oscillations but at different frequencies (tracings from A and B) than when recorded with a sensor that simultaneously acquires data from both regions appear intermixed (tracing from C).

Determination of the regularity index on these oscillations would reveal as many "peak" values as there are regular frequencies; in the example of FIG. 13, there are two regularity index values of 0.9 indicative of highly regular oscillations at two different frequencies that when recorded with a single electrode that spans both sub-regions, appear as an "admixture" with two high regularity index values. The implication, for therapeutic purposes, of having two or more high regularity index values (instead of a single one) in a time window, is that unless modified or "subsumed" into a single highly regular frequency, two or more energy pulses properly timed, may be desirable to treat the two or more oscillations.

FIG. 7 shows a flowchart depiction of a method, in accordance with one illustrative embodiment of the present disclosure. FIG. 7 has some elements in common with FIG. 6, and those common elements need not be described again.

FIG. 7 shows, after determining a degree of regularity at 615, a further step is taken at 720 to determine if there are epileptic oscillations at other frequencies with multiple degrees of regularity.

This point may be illuminated by reference to FIG. 12A-12B. These figures show a large circle depicting a neural structure (e.g., the brain, one of its lobes, a region within one of its lobes, or a sub-region within a region, etc.), whose activity is recorded at multiple sites (smaller circles or squares), spatial scales, and/or time scales. Regularity index values may differ or be similar between closely spaced regions with different cytoarchitecture or within a region with homogenous cytoarchitecture (FIG. 12A).

Multiple degrees of regularity may arise simultaneously or sequentially in different brain regions (e.g., regions A and B of FIG. 12A) or different brain sub-regions within the same region (e.g., subregions C and D of FIG. 12A).

If the determination at 720 finds there is only one degree of regularity for the patient's epileptic activity, a determination can be made whether it is inside a first range at 620, which may be followed by subsequently applying and/or modifying at 630 and/or 640.

If there are multiple degrees of regularity inside the first range, one or both of the following may be performed at 735. First, at least one of the degrees of regularity may be modified, similarly to the modifications discussed above at 640. For example, of the electrical activities depicted in FIG. 12A, activities in region B and subregion D could be made more regular. Second, multiple electrical stimulations may be applied. Each of the electrical stimulations applied at 735 may be chosen to treat one of the regular oscillations having a degree of regularity found at 720. Continuing the example of FIG. 12A, one electrical stimulation or other therapy could be applied to treat the activity in region A, and a second electrical stimulation or other therapy could be applied to treat the activity in sub-region C.

As with the regularity index value, phase locking/alignment index values may differ or be similar between closely spaced regions with different cytoarchitecture or within a region with homogenous cytoarchitecture (FIG. 12B).

FIG. 8 shows a flowchart depiction of a method, in accordance with one illustrative embodiment of the present disclosure. In the depicted embodiment, an epileptic event, including its number of origin sites, may be detected in at least one brain region of a patient, at 810. Detecting the epileptic event may be performed using any technique discussed herein. Determination of the number of epileptogenic sites or loci may then be made at 820.

However, if there are multiple origin sites, the degree of regularity at each site may be determined at 830. Techniques for doing so have been described elsewhere herein. As discussed above and shown in FIG. 12A, multiple degrees of regularity may arise simultaneously or sequentially in different brain regions or different brain sub-regions within the same region.

It may be determined at 850 whether the degrees of regularity are each within a first range. For example, FIG. 12B depicts three oscillations, numbered 1-3, which are each highly regular. If the degrees of regularity are not all within the first range, then at least one or more of them may be modified at 852, making use of techniques described elsewhere herein. If the degrees of regularity are all within the first range (such as in the example shown in FIG. 12B), then a phase relationship between the epileptic activity at the multiple sites may be determined at 854. Whether the epileptic activity is phase-locked may be determined at 860. Continuing the example of FIG. 12B, all three of the oscillations 1-3 are phase-locked; the phase difference remains constant over a time period, such as the time between time α and time β. Phase aligned means two oscillations are phase locked, with negligible phase difference.

FIG. 13 shows another example of epileptic activity having two different frequencies but identical degrees of regularity as shown in regions A and B. Having found that the regularity indices in sub-regions A and B are within a first threshold, a decision may be made to determine their degree of phase locking before delivering therapy pulses; if the oscillations in both regions are phase-locked and there is also substantial phase alignment between the two frequencies, therapy pulses may be delivered synchronously to both regions. If they are phase locked but not aligned, therapy pulses with differences in the timing of delivery reflective of the phase difference between the two frequencies may be delivered or modification (e.g. alignment) pulses may be applied before delivery of therapy pulses if the oscillations' conditions warrant it.

Returning to FIG. 8, the determination at 860 may find the epileptic activity is not phase-locked. If so, a phase-locking stimulus may be delivered at 862.

On the other hand, if the determination at 860 finds the epileptic activity is phase-locked, it may still be not amenable to treatment with a single treatment stimulation. For example, in FIG. 12B, one treatment stimulation about one-third of a wavelength after α would be likely to terminate oscillations 2 and 3, but would be unlikely to terminate oscillation 1. Thus, a determination as to whether the epileptic activity is phase-aligned may be made at 870.

From the determination at 870, it may be found the epileptic activity at the various sites is phase-aligned. In this situation, a single treatment stimulation that is conducive to treating the epileptic activity at one site may also be conducive to treating it at the other sites. Thus, a treatment stimulation may be delivered at 874.

On the other hand, the determination at 870 may find the epileptic activity at the various sites is not phase-aligned. It is phase-locked, meaning that a plurality of treatment stimulations, one for each locked phase, may be delivered at 872, preferably as much out of phase from one another as the various epileptic activity tracings are out of phase from one another. For example, in FIG. 12B, one treatment stimulation at about α would be likely to terminate oscillation 1, and a second treatment stimulation about one-third of a wavelength after α would be likely to terminate oscillations 2 and 3, thus terminating all three oscillations.

Alternatively or in addition, a phase-aligning stimulation may be delivered at 872, such that the epileptic activity at the various sites comes into phase alignment.

FIG. 9 shows a flowchart depiction of a method, in accordance with one illustrative embodiment of the present disclosure. In the depicted method, an epileptic event in at least a first brain region of a patient may be detected at 912. The regularity of electrical activity relating to the epileptic event in the first brain region may be modified at 918, if necessary (e.g., if it is outside a first range). At least one electrical stimulation pulse may be applied to at least a first neural target of the patient for reducing said electrical activity relating to said epileptic event, at 930. Detecting the epileptic event, increasing regularity of electrical activity, and applying at least one electrical stimulation pulse may be performed using any technique(s) discussed herein.

Upon application of at least one electrical stimulation pulse to the at least first neural target, a response of the epileptic event to the electrical stimulation may be assessed at 950. Assessment of the response may be performed using any technique(s) discussed herein. In one embodiment, a body signal indicative of the epileptic event's response to the therapy may be received. In one embodiment, the body signal may be an autonomic signal. In another embodiment, the body signal may be a neurologic signal. In one embodiment, the body signal may be a metabolic signal. In another embodiment, the body signal may be an endocrine signal. In one embodiment, the body signal may be a tissue stress marker signal. In one embodiment, the body signal may be a cognitive signal. The body signal may be selected from one or more of the foregoing.

Exemplary autonomic signals that may be detected include, but are not limited to, a cardiac signal, skin resistance, a respiratory signal, an output (e.g., number of spikes/unit time; pattern of spikes, amplitude of spikes, etc.) from a parasympathetic or from sympathetic tissue, the patient's body temperature, or an infrared activity of a portion of the patient's body, among others.

Exemplary neurologic signals that may be detected include, but are not limited to, a motor activity signal, or a cognitive signal, among others.

Exemplary metabolic signals that may be detected include, but are not limited to, an arterial and/or venous blood pH, lactic acid concentration of the patient's blood, a pyruvic acid concentration of the patient's blood, or a potassium concentration of the patient's blood, among others.

Assessing the response at 950 may comprise determining whether the therapy gave an efficacious result against the epileptic event. An "efficacious result" may be demonstrated by a change in an efficacy index, an observation of improvement or termination of the epileptic event, or the like. In one embodiment, the assessment at 950 may comprise determining an efficacy index based upon a body signal.

A response may be assessed at any time. For example, a response may be assessed after applying the electrical therapy at 930 for a predetermined duration. For another example, a response may be assessed after applying the electrical therapy at 930 for less than a predetermined duration said predetermined duration being for example the duration of a therapy.

If the assessment reveals a beneficial change in the epileptic event at 960, e.g. a positive response, an efficacious result, a high and/or increased efficacy index, an improvement in the epileptic event, a termination of the epileptic event, or two or more thereof, delivery of the electrical stimulation pulse may be terminated at 990. Termination may alternatively or in addition be based upon at least one of exceeding a predetermined number of delivered electric stimulation pulses, exceeding a predetermined electrical stimulation duration, or exceeding a predetermined current density. Termination of a therapy may also occur in response to the determination that the therapy causes an adverse effect said effect including but not being limited to increasing the severity of a seizure and/or degrading any body system's function as determined using cerebral or extra-cerebral body signals, posing safety risks or causing intolerable effects.

If the therapy comprises at least one electrical pulse, terminating the therapy may comprise not delivering another pulse. Alternatively or in addition, terminating a therapy comprising at least one electrical pulse having a programmed pulse width may comprise terminating delivery of the electrical pulse prior to the end of the programmed pulse width.

The therapy may be continued indefinitely. In another embodiment, the therapy may be continued for a predetermined duration. The predetermined duration may be selected to result in termination of the application of the therapy after a safety duration, i.e., therapy may be terminated to reduce the likelihood of injury to the tissue to which the therapy is applied or to preserve battery life of a device, among other reasons. In another embodiment, if an adverse effect of the therapy is detected, application of the therapy may be terminated.

If a beneficial change in the epileptic event is not indicated, which may include no change in the epileptic event or an adverse effect of the therapy, the application of the therapy may be continued, as shown in FIG. 9 by the flow line from 960 to 930. For example, a lack of a beneficial change may be indicated by a finding an efficacy index may be less than an efficacy threshold, and the therapy may be continued in response to such a finding.

In one embodiment, if a beneficial change is not indicated, the therapy may be modified at 970. Modifying the therapy at 970 may comprise modifying at least one parameter of the therapy, such as (for an electrical therapy) a waveform, a pulse width, a number of pulses, an inter-pulse interval, an amplitude, a phase, a polarity, a timing of therapy delivery relative to a zero-crossing, a timing of the therapy delivery relative to an extremum, or a timing of the therapy delivery relative to a region of an ascending or descending slope of a neuronal oscillation, among others. Modifying the therapy at 970 may also comprise changing therapy modalities (e.g., from electrical to chemical, thermal, etc.). Modification of a therapy may also occur in response to the determination that the therapy causes an adverse effect said effect including but not being limited to increasing the severity of a seizure and/or degrading any body system's function as determined using cerebral or extra-cerebral body signals, posing safety risks or causing intolerable effects.

The modifying at 970 may comprise modifying the therapy as a function of at least one of an efficacy index value or a direction of change of an efficacy index value.

In other embodiments, modifying a therapy at 970 may be performed according to a predetermined schedule, in response to an external input, or both, alone or in combination with any other modifying technique.

In one embodiment, if the therapy has a predetermined duration, modifying the therapy at 970 may be performed prior to the end of the predetermined duration.

If modifying is performed at 970, the modified therapy may be delivered at 980. Thereafter, the assessing at 950, modifying at 970, and delivering at 980 may be repeated as needed, until a beneficial change is found at 960, or another ground for terminating delivery of the therapy arises.

Any method depicted in FIGS. 6-9 may be performed by a non-transitive, computer-readable storage device for storing instructions that, when executed by a processor, perform the method.

All of the methods and apparatuses disclosed and claimed herein may be made and executed without undue experimentation in light of the present disclosure. While the methods and apparatus of this disclosure have been described in terms of particular embodiments, it will be apparent to those skilled in the art that variations may be applied to the methods and apparatus and in the steps, or in the sequence of steps, of the method described herein without departing from the concept, spirit, and scope of the disclosure, as defined by the appended claims. It should be especially apparent that the principles of the disclosure may be applied to selected cranial nerves other than, or in addition to, the vagus nerve to achieve particular results in treating patients having epilepsy, depression, or other medical conditions.

The particular embodiments disclosed above are illustrative only. The disclosure may be modified and practiced in different but equivalent manners. Furthermore, no limitations are intended to the details of construction or design herein shown other than as described in the claims below. It is, therefore, evident that the particular embodiments disclosed above may be modified and all such variations are considered within the scope and spirit of the disclosure. Accordingly, the protection sought herein is as set forth in the claims below.

What is claimed:

1. A medical device, comprising:
an epileptic event detection module configured to detect an epileptic event;
at least one sensor configured to collect one or more electrical activity signals relating to the epileptic event from at least one region of a brain of a patient;
a regularization determination module configured to determine a first regularity index of the one or more electrical activity signals;
a neuronal regularization module configured to modify the first regularity index of an electrical activity in the at least one region of the brain of the patient;
a phase-locking determination module configured to determine a degree of phase-locking between a first electrical activity of a first brain region of the patient and a second electrical activity of a second brain region of the patient;
a phase-locking module configured to modify a first phase-locking index between the first electrical activity in the first brain region of the patient and the second electrical activity in the second brain region of the patient;
a stimulation module configured to apply a first electrical stimulation to a first neural target of the patient based on an indication of the epileptic event;
wherein the epileptic event detection module is configured to: detect a second electrical activity signal relating to an epileptic activity in the second brain region of the patient;
determining a second regularity index based on the second electrical activity signal; determine a second phase-locking index between the first brain region and the second brain region of the patient based on the first regularity index and the second regularity index being within a first range; and applying a second electrical stimulation to a second neural target of the patient for treating the epileptic activity, in response to the second phase-locking index being within a second range.

2. The medical device of claim 1, wherein the regularization determination module is configured to determine one or more regularity indexes based at least in part on at least one of an oscillation morphology of the electrical activity, an amplitude of the electrical activity, a frequency of the electrical activity, a frequency component of the electrical activity, a power level of the frequency component of the electrical activity, and a power spectral density of the electrical activity.

3. The medical device of claim 1, wherein the regularization determination module is configured to determine the first regularity index for a window comprising from two to twenty wavelengths of a predominant oscillation of the electrical activity.

4. The medical device of claim 1, wherein the regularization determination module is configured to determine one or more regularity indexes by an autocorrelation function of the electrical activity.

5. The medical device of claim 1, wherein the regularization determination module is configured to determine one or more regularity indexes based on at least one of a measure of autocorrelation, a measure of amplitude variance, a measure of frequency variance, a measure of zero-crossings interval variance, a measure of ascending and descending slope variances, a number of extrema, a polarity of extrema, a polynomial fitting to measure an error of polynomial approximation, a box counting method, a Lipschitz exponent of one of the foregoing, or a Holder exponent of one of the foregoing.

6. The medical device of claim 1, wherein the stimulation module is configured to apply at least one of the first electrical stimulation and the second electrical stimulation for a duration of less than about one-third of a dominant wavelength of the electrical activity.

* * * * *